(12) United States Patent
Mathur

(10) Patent No.: US 7,045,328 B2
(45) Date of Patent: *May 16, 2006

(54) PURIFIED THERMOSTABLE PYROCOCCUS FURIOSUS DNA POLYMERASE I

(75) Inventor: Eric J. Mathur, Solana Beach, CA (US)

(73) Assignee: Stratagene California, La Jolla, CA (US)

( * ) Notice: Subject to any disclaimer, the term of this patent is extended or adjusted under 35 U.S.C. 154(b) by 174 days.

This patent is subject to a terminal disclaimer.

(21) Appl. No.: 10/176,357

(22) Filed: Jun. 19, 2002

(65) Prior Publication Data

US 2006/0040370 A1    Feb. 23, 2006

Related U.S. Application Data

(63) Continuation of application No. 09/244,889, filed on Feb. 5, 1999, now Pat. No. 6,489,150, which is a continuation of application No. 07/803,627, filed on Dec. 2, 1991, now Pat. No. 5,948,663, which is a continuation-in-part of application No. 07/776,552, filed on Oct. 15, 1991, now abandoned, which is a continuation-in-part of application No. 07/657,073, filed on Feb. 19, 1991, now abandoned, which is a continuation-in-part of application No. 07/620,568, filed on Dec. 3, 1990, now abandoned.

(51) Int. Cl.
*C12N 15/54* (2006.01)
*C12N 9/12* (2006.01)

(52) U.S. Cl. ............... 435/194; 435/320.1; 435/252.3; 435/325; 536/23.2

(58) Field of Classification Search ............ 435/320.1, 435/194, 252.3, 325; 536/23.2, 23.1, 24.3, 536/24.22
See application file for complete search history.

(56) References Cited

U.S. PATENT DOCUMENTS

| | | | |
|---|---|---|---|
| 4,889,818 A | 12/1989 | Gelfand et al. | 435/194 |
| 4,994,372 A | 2/1991 | Tabor et al. | 435/6 |
| 5,210,036 A | 5/1993 | Comb et al. | 435/194 |
| 5,242,818 A | 9/1993 | Oshima et al. | 435/194 |
| 5,322,785 A | 6/1994 | Comb et al. | 435/194 |
| 5,352,778 A | 10/1994 | Comb et al. | 536/23.2 |

OTHER PUBLICATIONS

Bernad, et al., "A Conserved 3'-5' Exonuclease Active Site in Prokaryotic and Eukaryotic DNA Polymerases," *Cell*, 59:219-228 (1989).
Berger, et al., "Guide to Molecular Cloning Techniques," *Meth. in Enzymol.*, 152:393-399; 415-423, 432-449, 661-704 (1987).
Blanco, et al., "Evidence favouring the hypothesis of a conserved 3'-5' exonuclease active site in DNA-dependent DNA polymerases," *Gene*, 112:139-144 (1992).
Bryant, et al., *J. Biol. Chem.*, 264:5070-5079 (1989).
Deutscher, "Guide to Protein Purification," *Meth. in Enzymol.*, 182:738-751 (1990).
Dutton, et al., "General method for amplifying regions of very high G+C content," *Nucl. Acids Res.*, 2953-2954 (1993).
Eckert, et al., *Nucl. Acids Res.*, 18:3739-3744 (1990).
Ennis, et al., *Proc Natl. Acad. Sci. USA*, 87:2833-2837 (1990).
Forterre P., *Nucl. Acids. Res.*, 20(7):1811 (1992).
Hamal, Abdellah et al., "Purification and Characterization of a DNA polymerase from the Archaebacterium *Thermoplasma Acidophilum*," *Eur. J. Biochem.*, 190(3):517-21 (1990).
Keohavong, et al., *Proc. Natl. Acad. Sci. USA*, 86:9253-9257 (1989).
Kohler, et al., *Proc. Natl. Acad. Sci. USA*, 88:7958-7962 (1991).
Klimczak, Leszek J., et al., "Purification and Characterization of DNA Polymerase from the Archaebacterium *Sulfolobus acidocalarius*," *Nucleic Acids Research*, 13(14):5269-82 (1985).
Klimczak, Lescek J., et al., "Purification and Characterization of DNA Polymerase from the Archaebacterium *Methanobacterium thermoautotrophicum*," *Biochemistry*, 25:4850-55 (1986).
lawyer, F.C. et al. "Isolation Characterization and Expression in *E. coli* of the DNA Polymerase Gene From *Thermus agriaticus*," *J. Biol. Chem.*, 264(11): 6427-6437 (1989).
Lee, J., *Laboratory Methods*, Alternative Dideoxy Sequencing of Double-Stranded DNA by Cyclic Reactions Using Taq Polymerase, *DNA and Cell Biology*, 10(1):67-73 (1991).
Lundberg, et al., *FASEBJ* 5(6) A1549 (1991).
Lundberg KS, et al., "High-fidelity amplification using a thermostable DNA Polymerase isolated from *Pyrococcus furiosus*," *Gene*, Dec. 1, 1991; 108(1):1-6.
Mathur, et al., *J. Cell. Biochem.*, 16B:29 (1992).
Mathur, et al., *Nuc. Acids. Res.*, 19(24):6952 (1991).
Perrino, et al., *Biochemistry*, 29:5226-5231 (1990).
Reiss, et al., *Nucleic Acids Res.*, 18:973-978 (1990).

(Continued)

*Primary Examiner*—Rebecca Prouty
(74) *Attorney, Agent, or Firm*—Finnegan, Henderson, Farabow, Garrett & Dunner, LLP

(57) ABSTRACT

Purified thermostable *Pyrococcus furiosus* DNA polymerase that migrates on a non-denaturing polyacrylamide gel faster than phosphorylase B and Taq polymerase and more slowly than bovine serum albumin and has an estimated molecular weight of 90,000–93,000 daltons when compared with a Taq polymerase standard assigned a molecular weight of 94,000 daltons.

5 Claims, 1 Drawing Sheet

OTHER PUBLICATIONS

Rossi, M. et al, "Structure and Properties of Thermophilic and Thermostable DNA polymerase Isolated from *Sulfolobus solfataricus*," *System Appl. Microbiol*, 7:337-341 (1986).

Ruttimann, Carmen et al., "DNA Polymerases from the Extremely Thermophilic Bacterium," *Thermus thermophilus* HB-8, *Eur. J. Biochem.*, 149 (1):41-46 (1985).

Saiki, et al., *Science*, 239:487-491 (1988).

Simpson, H.D., et al., Purification of a Thermostable DNA Polymerase from a *Thermotoga* Species, *Ann. N.Y. Acad. Sci.*, 613:426-428 (1990).

Tindall, et al., *Biochemistry*, 27:6008-6013 (1988).

Wahl, G. M. et al, "Molecular Hybridization of Immobilized Nucleic Acids: Theoretical Concepts and Practical Considerations," *Methods in Enzymology*, 152:399-412 (1987).

Ward, John M., et al., "Phosphocellulose as a Tool for Rapid Purification of DNA-modifying Enzymes," *Analytica Chimica Acta*, 249:195-200 (1990).

Wheelis, et al., "On the nature of global classification," *Proc. Natl. Acad. Sci.*, 89:2930-2934 (1992).

SEQUENCE LISTING

<160> NUMBER OF SEQ ID NOS: 6

<210> SEQ ID NO 1
<211> LENGTH: 775
<212> TYPE: PRT
<213> ORGANISM: Pyrococcus furiosus

<400> SEQUENCE: 1

Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
        35                  40                  45

Glu Glu Val Lys Lys Ile Thr Gly Glu Arg His Gly Lys Ile Val Arg
    50                  55                  60

Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Val Pro Thr Ile
                85                  90                  95

Arg Glu Lys Val Arg Glu His Pro Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Leu Lys Ile Leu Ala Phe Asp Ile Glu Thr
    130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

Asp Leu Pro Tyr Val Glu Val Val Ser Ser Glu Arg Glu Met Ile Lys
            180                 185                 190

Arg Phe Leu Arg Ile Ile Arg Glu Lys Asp Pro Asp Ile Ile Val Thr
        195                 200                 205

Tyr Asn Gly Asp Ser Phe Asp Phe Pro Tyr Leu Ala Lys Arg Ala Glu

-continued

```
            210                 215                 220
Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Thr Arg Thr Ile Asn Leu Pro Thr
                260                 265                 270

Tyr Thr Leu Glu Ala Val Tyr Glu Ala Ile Phe Gly Lys Pro Lys Glu
            275                 280                 285

Lys Val Tyr Ala Asp Glu Ile Ala Lys Ala Trp Glu Ser Gly Glu Asn
290                 295                 300

Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
                325                 330                 335

Val Gly Gln Pro Leu Trp Asp Val Ser Arg Ser Thr Gly Asn Leu
                340                 345                 350

Val Glu Trp Phe Leu Leu Arg Lys Ala Tyr Glu Arg Asn Glu Val Ala
            355                 360                 365

Pro Asn Lys Pro Ser Glu Glu Glu Tyr Gln Arg Arg Leu Arg Glu Ser
    370                 375                 380

Tyr Thr Gly Gly Phe Val Lys Glu Pro Glu Lys Gly Leu Trp Glu Asn
385                 390                 395                 400

Ile Val Tyr Leu Asp Phe Arg Ala Leu Tyr Pro Ser Ile Ile Ile Thr
                405                 410                 415

His Asn Val Ser Pro Asp Thr Leu Asn Leu Glu Gly Cys Lys Asn Tyr
                420                 425                 430

Asp Ile Ala Pro Gln Val Gly His Lys Phe Cys Lys Asp Ile Pro Gly
            435                 440                 445

Phe Ile Pro Ser Leu Leu Gly His Leu Leu Glu Glu Arg Gln Lys Ile
    450                 455                 460

Lys Thr Lys Met Lys Glu Thr Gln Asp Pro Ile Glu Lys Ile Leu Leu
465                 470                 475                 480

Asp Tyr Arg Gln Lys Ala Ile Lys Leu Leu Ala Asn Ser Phe Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Lys Tyr Ile Glu Leu Val Trp Lys Glu
    515                 520                 525

Leu Glu Glu Lys Phe Gly Phe Lys Val Leu Tyr Ile Asp Thr Asp Gly
    530                 535                 540

Leu Tyr Ala Thr Ile Pro Gly Gly Glu Ser Glu Glu Ile Lys Lys Lys
545                 550                 555                 560

Ala Leu Glu Phe Val Lys Tyr Ile Asn Ser Lys Leu Pro Gly Leu Leu
                565                 570                 575

Glu Leu Glu Tyr Glu Gly Phe Tyr Lys Arg Gly Phe Phe Val Thr Lys
            580                 585                 590

Lys Arg Tyr Ala Val Ile Asp Glu Glu Gly Lys Val Ile Thr Arg Gly
            595                 600                 605

Leu Glu Ile Val Arg Arg Asp Trp Ser Glu Ile Ala Lys Glu Thr Gln
        610                 615                 620

Ala Arg Val Leu Glu Thr Ile Leu Lys His Gly Asp Val Glu Glu Ala
625                 630                 635                 640
```

```
Val Arg Ile Val Lys Glu Val Ile Gln Lys Leu Ala Asn Tyr Glu Ile
            645                 650                 655

Pro Pro Glu Lys Leu Ala Ile Tyr Glu Gln Ile Thr Arg Pro Leu His
            660                 665                 670

Glu Tyr Lys Ala Ile Gly Pro His Val Ala Val Ala Lys Lys Leu Ala
            675                 680                 685

Ala Lys Gly Val Lys Ile Lys Pro Gly Met Val Ile Gly Tyr Ile Val
            690                 695                 700

Leu Arg Gly Asp Gly Pro Ile Ser Asn Arg Ala Ile Leu Ala Glu Glu
705                 710                 715                 720

Tyr Asp Pro Lys Lys His Lys Tyr Asp Ala Glu Tyr Tyr Ile Glu Asn
            725                 730                 735

Gln Val Leu Pro Ala Val Leu Arg Ile Leu Glu Gly Phe Gly Tyr Arg
            740                 745                 750

Lys Glu Asp Leu Arg Tyr Gln Lys Thr Arg Gln Val Gly Leu Thr Ser
            755                 760                 765

Trp Leu Asn Ile Lys Lys Ser
    770                 775

<210> SEQ ID NO 2
<211> LENGTH: 3499
<212> TYPE: DNA
<213> ORGANISM: Pyrococcus furiosus
<220> FEATURE:
<221> NAME/KEY: misc_feature
<222> LOCATION: (1)..(3499)
<223> OTHER INFORMATION: n is any nucleotide

<400> SEQUENCE: 2
ccctggtcct gggtccacat atatgttctt actcgccttt atgaagaatc ccccagtcgc      60
tctaacctgg gttatagtga caaatcttcc tccaccaccg cccaagaagg ttatttctat     120
caactctaca cctcccctat tttctctctt atgagatttt taagtatagt tatagagaag     180
gttttatact ccaaactgag ttagtagata tgtggggagc ataatgattt tagatgtgga     240
ttacataact gaagaaggaa aacctgttat taggctattc aaaaaagaga acggaaaatt     300
taagatagag catgtagaa cttttagacc atacatttac gctcttctca gggatgattc     360
aaagattgaa gaagttaaga aaataacggg ggaaaggcat ggaaagattg tgagaattgt     420
tgatgtagag aaggttgaga aaagtttct cggcaagcct attaccgtgt ggaaacttta     480
tttggaacat ccccaagatg ttcccactat tagagaaaaa gttagagaac atccagcagt     540
tgtggacatc ttcgaatacg atattccatt tgcaaagaga tacctcatcg acaaaggcct     600
aataccaatg gagggggaag aagagctaaa gattcttgcc ttcgatatag aaaccctcta     660
tcacgaagga gaagagtttg aaaaggccc aattataatg attagttatg cagatgaaaa     720
tgaagcaaag gtgattactt ggaaaaacat agatcttcca tacgttgagg ttgtatcaag     780
cgagagagag atgataaaga gatttctcag gattatcagg gagaaggatc ctgacattat     840
agttacttat aatggagact cattcgactt cccatatttca gcgaaagggg cagaaaaact     900
tgggattaaa ttaaccattg aagagatgg aagcgagccc aagatgcaga gaataggcga     960
tatgacggct gtagaagtca aggaagaat acatttcgac ttgtatcatg taataacaag    1020
gacaataaat ctcccaacat acacactaga ggctgtatat gaagcaattt ttggaaagcc    1080
aaaggagaag gtatacgccg acgagatagc aaaagcctgg gaaagtggag agaaccttga    1140
gagagttgcc aaatactcga tggaagatgc aaaggcaact tatgaactcg ggaaagaatt    1200
```

```
ccttccaatg gaaattcagc tttcaagatt agttggacaa cctttatggg atgtttcaag    1260
gtcaagcaca gggaaccttg tagagtggtt cttacttagg aaagcctacg aaagaaacga    1320
agtagctcca acaagccaag gtgaagagga gtatcaaaga aggctcaggg agagctacac    1380
aggtggattc gttaaagagc cagaaaaggg gttgtgggaa acatagtat  acctagattt    1440 tagagcccta tatccctcga ttataattac ccacaatgtt tctcccgata ctctaaatct    1500
tgagggatgc aagaactatg atatcgctcc tcaagtaggc cacaagttct gcaaggacat    1560
ccctggtttt ataccaagtc tcttgggaca tttgttagag gaaagacaaa agattaagac    1620
aaaaatgaag gaaactcaag atcctataga aaaaatactc cttgactata gacaaaaagc    1680
gataaaactc ttagcaaatt cttcctacgg atattatggc tatgcaaaag caagatggta    1740
ctgtaaggag tgtgctgaga gcgttactgc ctggggaaga aagtacatcg agttagtatg    1800
gaaggagctc gaagaaaagt ttggatttaa agtcctctac attgacactg atggtctcta    1860
tgcaactatc ccaggaggag aaagtgagga aataaagaaa aaggctctag aatttgtaaa    1920
atacataaat tcaagctccc tggactgct  agagcttgaa tatgaagggt tttataagag    1980
gggattcttc gttacgaaga agaggtatgc agtaatagat gaagaaggaa aagtcattac    2040
tcgtggttta gagatagtta ggagagattg gagtgaaatt gcaaaagaaa ctcaagctag    2100
agttttggag acaatactaa acacggaga  tgttgaagaa gctgtgagaa tagtaaaaga    2160
agtaatacaa aagcttgcca attatgaaat tccaccagag aagctcgcaa tatatgagca    2220
gataacaaga ccattacatg agtataaggc gataggtcct cacgtagctg ttgcaaagaa    2280
actagctgct aaaggagtta aaataaagcc aggaatggta attggataca tagtacttag    2340
aggcgatggt ccaattagca ataggggcaat tctagctgag gaatacgatc ccaaaaagca    2400
caagtatgac gcagaatatt acattgagaa ccaggttctt ccagcggtac ttaggatatt    2460 ggagggatttt ggatacagaa aggaagacct cagataccaa aagacaagac aagtcggcct    2520
aacttcctgg cttaacatta aaaaatccta gaaaagcgat agatatcaac ttttattctt    2580
tctaaccttt ttctatgaaa gaagaactga gcaggaatta ccagttcttc cgttatttta    2640
tgggtaatta aaaacccatg ctcttgggag aatcttcgaa taaaatccct aacttcaggc    2700
tttgctaagt gaatagaata acaacatca ctcacttcaa acgccttcgt tagaaatggt    2760
ctatctgcat gcttctctgg ctcggaanng gaggattcat aacaacagta tcaacattct    2820
cagagaattg agaaacatca gaaactttga cttctacaac atttctaact ttgcaactct    2880
tcaagatttt ctaaaagaat tttaacggcc tcctcgtcaa tttcgacgac gtagatcttt    2940
tttgctccaa gcagagccgc tccaatggat aacaccctg  ttcccgcacc caagtccgct    3000
acaatttttt ccttgtatct cctaatgtat aagcaagcca aaggagagta gatgctacct    3060
ttccgggagt tttgtattgc tctagccaag gtttgggatt tttgaatcct ttaactctgg    3120
aaagtataat ttcaagctcc ttcttcttca tgacagatga aaaattgttt tgtctctttt    3180
taacttttac agaaataact gtctcaaatt atgacaactc ttgacatttt tacttcatta    3240
ccagggtaat gttttaagt  atgaaatttt tctttcatag aggaggnnnn nngtcctctc    3300
ctcgatttcc ttggttgtgc tccatatgat aagcttccaa agtgggtgtt cagactttta    3360
gacactcaaa taccagacga caatggtgtg ctcactcaag ccccatatgg gttgagaaaa    3420
gtagaagcgg cactactcag atgcttcccc aggaatgagg ttgttgtagc tcntcccnga    3480
aagattgaga tgttccttgg                                               3499
```

```
<210> SEQ ID NO 3
<211> LENGTH: 20
<212> TYPE: DNA
<213> ORGANISM: Pyrococcus furiosus
<220> FEATURE:
<221> NAME/KEY: misc_feature
<222> LOCATION: (9)..(9)
<223> OTHER INFORMATION: n is inosine or cytosine
<220> FEATURE:
<221> NAME/KEY: misc_feature
<222> LOCATION: (15)..(15)
<223> OTHER INFORMATION: n is inosine
<220> FEATURE:
<221> NAME/KEY: misc_feature
<222> LOCATION: (18)..(18)
<223> OTHER INFORMATION: n is inosine

<400> SEQUENCE: 3
kaytahatna ccgangangg                                            20

<210> SEQ ID NO 4
<211> LENGTH: 20
<212> TYPE: DNA
<213> ORGANISM: Pyrococcus furiosus
<220> FEATURE:
<221> NAME/KEY: misc_feature
<222> LOCATION: (9)..(9)
<223> OTHER INFORMATION: n is inosine
<220> FEATURE:
<221> NAME/KEY: misc_feature
<222> LOCATION: (12)..(12)
<223> OTHER INFORMATION: n is inosine

<400> SEQUENCE: 4
ccytcytcng tnatrtartc                                            20

<210> SEQ ID NO 5
<211> LENGTH: 14
<212> TYPE: DNA
<213> ORGANISM: Pyrococcus furiosus

<400> SEQUENCE: 5
ttyaaraara aygg                                                  14

<210> SEQ ID NO 6
<211> LENGTH: 14
<212> TYPE: DNA
<213> ORGANISM: Pyrococcus furiosus

<400> SEQUENCE: 6
ccrttyttyt traa                                                  14
```

PURIFIED THERMOSTABLE *PYROCOCCUS FURIOSUS* DNA POLYMERASE I

CROSS REFERENCE TO RELATED APPLICATION

This application is a continuation of U.S. application Ser. No. 09/244,889, filed Feb. 5, 1999, now U.S. Pat. No. 6,489,150, which is a continuation of application U.S. application Ser. No. 07/803,627, filed Dec. 2, 1991, now U.S. Pat. No. 5,948,663, which is a continuation-in-part of U.S. application Ser. No. 07/776,552, filed Oct. 15, 1991, now abandoned, which is a continuation-in-part of U.S. application Ser. No. 07/657,073, filed Feb. 19, 1991 now abandoned, which is continuation-in-part of U.S. application Ser. No. 07/620,568, filed Dec. 3, 1990, now abandoned. U.S. application Ser. No. 09/244,889 is being relied upon and is incorporated herein by reference.

TECHNICAL FIELD

The present invention relates to a thermostable enzyme having DNA polymerase I activity useful in nucleic acid synthesis by primer extension reaction.

Background

The archaebacteria are a recently discovered group of microorganisms that grow optimally at temperatures above 80° C. Some 20 species of these extremely thermophilic bacteria-like organisms have been isolated, mainly from shallow submarine and deep sea geothermal environments. Most of the archaebacteria are strict anaerobes and depend on the reduction of elemental sulfur for growth.

The archaebacteria include a group of "hyperthermophiles" that grow optimally around 100° C. These are presently represented by three distinct genera, *Pyrodictium, Pyrococcus*, and *Pyrobaculum. Phyodictium brockii* ($T_{opt}$ 105° C.) is an obligate autotroph which obtains energy be reducing $S^O$ to $H_2S$ with $H_2$, while *Pyrobaculum islandicum* ($T_{opt}$ 100° C.) is a facultative heterotroph that uses either organic substrates or $H_2$ to reduce $S^O$. In contrast, *Pyrococcus furiosus* ($T_{opt}$ 100° C.) grows by a fermentative-type metabolism rather than by $S^O$ respiration. It is a strict heterotroph that utilizes both simple and complex carbohydrates where only $H_2$ and $CO_2$ are the detectable products. The organism reduces elemental sulfur to $H_2S$ apparently as a form of detoxification since $H_2$ inhibits growth.

The discovery of microorganisms growing optimally around 100° C. has generated considerable interest in both academic and industrial communities. Both the organisms and their enzymes have the potential to bridge the gap between biochemical catalysis and many industrial chemical conversions. However, knowledge of the metabolism of the hyperthermophilic microorganisms is presently very limited.

The polymerase chain reaction (PCR) is a powerful method for the rapid and exponential amplification of target nucleic acid sequences. PCR has facilitated the development of gene characterization and molecular cloning technologies including the direct sequencing of PCR amplified DNA, the determination of allelic variation, and the detection of infectious and genetic disease disorders. PCR is performed by repeated cycles of heat denaturation of a DNA template containing the target sequence, annealing of opposing primers to the complementary DNA strands, and extension of the annealed primers with a DNA polymerase. Multiple PCR cycles result in the exponential amplification of the nucleotide sequence delineated by the flanking amplification primers.

An important modification of the original PCR technique was the substitution of *Thermus aquaticus* (Taq) DNA polymerase in place of the Klenow fragment of *E. coli* DNA pol I (Saiki, et al. *Science*, 230:1350–1354 (1988)). The incorporation of a thermostable DNA polymerase into the PCR protocol obviates the need for repeated enzyme additions and permits elevated annealing and primer extension temperatures which enhance the specificity of primer:template associations. Taq polymerase thus serves to increase the specificity and simplicity of PCR.

Although Taq polymerase is used in the vast majority of PCR performed today, it has a fundamental drawback: purified Taq DNA polymerase enzyme is devoid of 3' to 5' exonuclease activity and thus cannot excise misinserted nucleotides (Tindall, et al., *Biochemistry*, 29:5226–5231 (1990)). Several independent studies suggest that 3' to 5' exonuclease-dependent proofreading enhances the fidelity of DNA synthesis. Reyland et al, *J. Biol. Chem.*, 263:6518–6524, 1988; Kunkel et al, *J. Biol. Chem.*, 261:13610–13616, 1986; Bernad et al, *Cell*, 58:219–228, 1989. Consistent with these findings, the observed error rate (mutations per nucleotide per cycle) of Taq polymerase is relatively high; estimates range from $2 \times 10^{-4}$ during PCR (Saiki et al., *Science*, 239:487–491 (1988); Keohavaong et al. *Proc. Natl. Acad. Sci. USA*, 86:9253–9257 (1989)) to $2 \times 10^{-5}$ for base substitution errors produced during a single round of DNA synthesis of the lacZ gene (Eckert et al., *Nucl. Acids Res.*, 18:3739–3744 (1990)).

Polymerase induced mutations incurred during PCR increase arithmetically as a function of cycle number. For example, if an average of two mutations occur during one cycle of amplification, 20 mutations will occur after 10 cycles and 40 will occur after 20 cycles. Each mutant and wild type template DNA molecule will be amplified exponentially during PCR and thus a large percentage of the resulting amplification products will contain mutations. Mutations introduced by Tag polymerase during DNA amplification have hindered PCR applications which require high fidelity DNA synthesis.

SUMMARY OF THE INVENTION

A thermostable DNA polymerase from the hyperthermophilic, marine archaebacterium, *Pyrococcus furiosus* (Pfu) has been discovered. The monomeric, multifunctional enzyme possesses both DNA polymerase and 3' to 5' exonuclease activities. The polymerase is extremely thermostable with a temperature optimum near 75° C. The purified enzyme functions effectively in the polymerase chain reaction (PCR). In addition, results from PCR fidelity studies indicate that *Pyrococcus furiosus* DNA polymerase yields amplification products containing 12 fold less mutations than reaction products from similar amplifications performed with Taq DNA polymerase. The 3' to 5' exonuclease dependent proofreading activity of Pfu DNA polymerase will excise mismatched 3' terminal nucleotides from primer:template complexes and correctly incorporate nucleotides complementary to the template strand.

Unlike Taq DNA polymerase, Pfu DNA polymerase does not possess 5' to 3' exonuclease activity. Pfu, like Taq and Vent polymerases, does exhibit a polymerase dependent 5' to 3' strand displacement activity. Pfu DNA polymerase remains greater that 95% active after one hour incubation at 95° C. In contrast, Vent polymerase [New England Biolabs (NEB) Beverly, Mass.] looses greater than 50% of its polymerase activity after one hour incubation at 95° C. Pfu DNA polymerase is thus unexpectedly superior to Taq and Vent DNA polymerases in amplification protocols requiring high fidelity DNA synthesis.

Thus, the present invention contemplates a purified thermostable *P. furiosus* DNA polymerase I (Pfu DNA Pol I or Pyro polymerase) having an amino terminal amino acid residue sequence represented by the formula shown in SEQ ID NO 1, having 775 amino acid residues.

The apparent molecular weight of the native protein is about 90,000–93,000 daltons as determined by SDS-PAGE under non-denaturing (non-reducing) conditions using Taq polymerase as a standard having a molecular weight of 94,000 daltons. In preferred embodiments, the Pyro polymerase is isolated from *P. furiosus*, and more preferably has a specific 3' to 5' exonuclease activity.

BRIEF DESCRIPTION OF THE DRAWINGS

In the drawings forming a portion of this disclosure.

DETAILED DESCRIPTION OF THE INVENTION

A. Definitions

Figure 1:
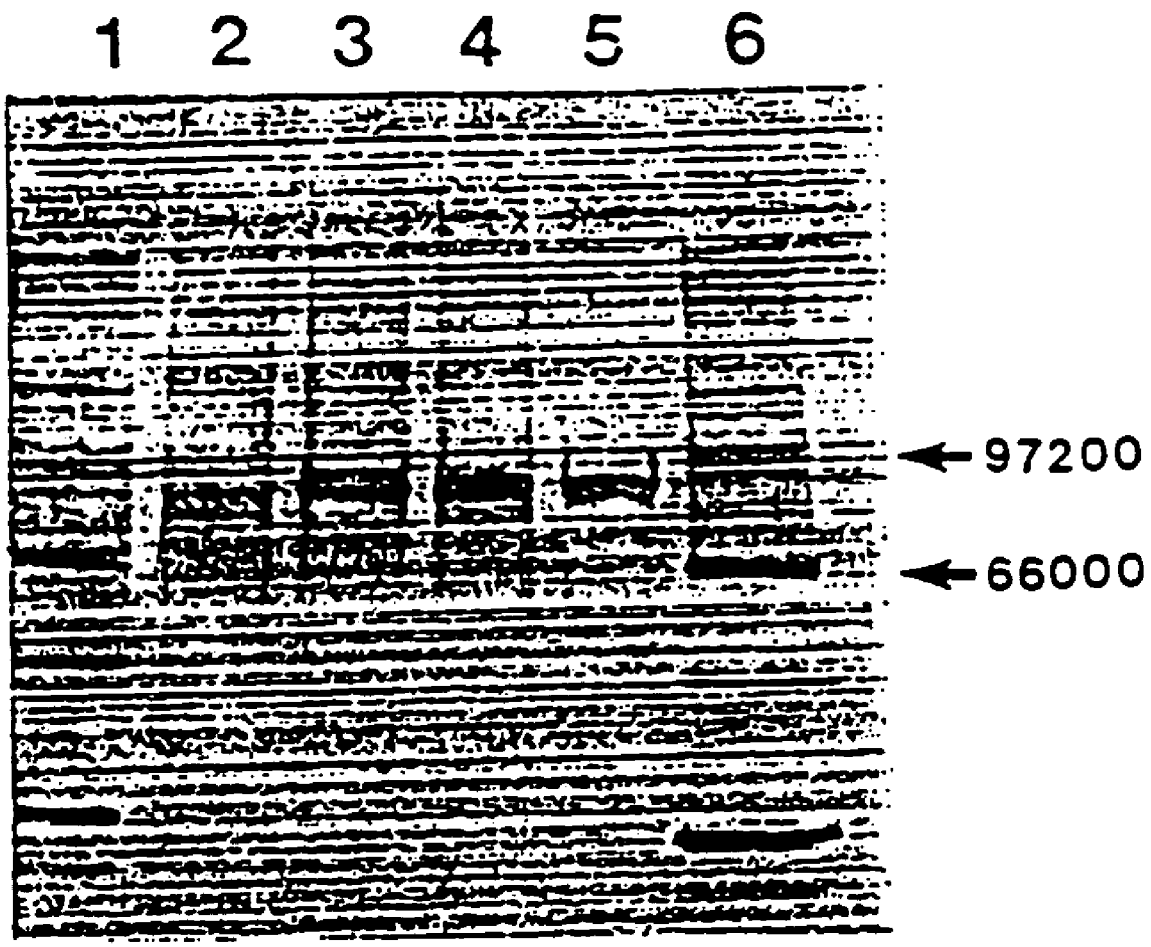
FIG. 1 illustrates the molecular weight determination of Pyro DNA polymerase compared to Taq DNA polymerase by SDS-PAGE analysis (8–16% gradient gel, under non-reducing conditions). High molecular weight standards (Sigma Chem. Co., St. Louis, Mo.) are electrophoresed in lanes 1 and 6. The molecular weights of Phosphorylase B (97,200 daltons) and bovine serum albumin (66,000 daltons) in lane 6 are indicated by arrows. Sequencing grade Taq DNA polymerase which has been modified (Promega Biotech, Madison, Wis.) has an apparent molecular weight of 80,000 daltons (lane 2). Taq DNA polymerases from Cetus (Emeryville, Calif.) and Stratagene (La Jolla, Calif.) are electrophoresed in lanes 3 and 4, respectively, each with an apparent molecular weight of 94,000 daltons. In lane 5, Pyro DNA polymerase exhibits a molecular weight of 90,000–93,000 daltons.

As used herein, "cell", "cell line", and "cell culture" can be used interchangeably and all such designations include progeny. Thus, the words "transformants" or "transformed cells" includes the primary subject cell and cultures derived therefrom without regard for the number of transfers. It is also understood that all progeny may not be precisely identical in DNA content, due to deliberate or inadvertent mutations. Mutant progeny that have the same functionality as screened for in the originally transformed cell are included.

The term "control sequences" refers to DNA sequences necessary for the expression of an operably linked coding sequence in a particular host organism. The control sequences that are suitable for procaryotes, for example, include a promoter, optionally an operator sequence, a ribosome binding site, and the like. Eucaryotic cells are known to utilize promoters, polyadenylation signals, and enhancers.

The term "expression system" refers to DNA sequences containing a desired coding sequence and control-sequences in operable linkage, so that hosts transformed with these sequences are capable of producing the encoded proteins. In order to effect transformation, the expression system may be included on a vector; however, the relevant DNA may then also be integrated into the host chromosome.

The term "gene" as used herein refers to a DNA sequence that encodes a polypeptide.

"Operably linked" refers to juxtaposition such that the normal function of the components can be performed. Thus, a coding sequence "operably linked" to control sequences refers to a configuration wherein the coding sequences can be expressed under the direction of the control sequences.

The term "oligonucleotide" as used herein is defined as a molecule comprised of two or more deoxyribonucleotides and/or ribonucleotides, preferably more than three. Its exact size will depend on many factors, which in turn depend on the ultimate function or use of the oligonucleotide. The oligonucleotide may be derived synthetically or by cloning.

The term "primer" as used herein refers to an oligonucleotide, whether occurring naturally or produced synthetically, which is capable of acting as a point of initiation of nucleic acid synthesis when placed under conditions in which synthesis of a primer extension product which is complementary to a nucleic acid strand is induced, i.e., in the presence of four different nucleotide triphosphates and thermostable enzyme in an appropriate buffer ('buffer" includes pH, ionic strength, cofactors, etc.) and at a suitable temperature. For Pyro polymerase, the buffer herein preferably contains 1.5–2 mM of a magnesium salt, preferably $MgCl_2$, 150–200 µM of each nucleotide, and 1 uM of each primer, along with preferably 50 mM KCl, 20 mM Tris buffer, pH 8–8.4, and 100 µg/ml gelatin.

The primer is preferably single-stranded for maximum efficiency in amplification, but may alternatively be double-stranded. If double-stranded, the primer is first treated to separate its strands before being used to prepare extension products. Preferably, the primer is an oligodeoxyribonucleotide. The primer must be sufficiently long to prime the synthesis of extension products in the presence of the thermostable enzyme. The exact lengths of the primers will depend on many factors, including temperature, source of primer and use of the method. For example, depending on the complexity of the target sequence, the oligonucleotide primer typically contains 15–25 nucleotides, although it may contain more or few nucleotides. Short primer molecules generally require colder temperatures to form sufficiently stable hybrid complexes with template.

The primers herein are selected to be "substantially" complementary to the different strands of each specific sequence to be amplified. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to be amplified to hybridize therewith and thereby form a template for synthesis of the extension product of the other primer. However, for detection purposes, particularly using labeled sequence-specific probes, the primers typically have exact complementarity to obtain the best results.

As used herein, the term "thermostable enzyme" refers to an enzyme which is stable to heat and is heat resistant and catalyzes (facilitates) combination of the nucleotides in the proper manner to form the primer extension products that are complementary to each nucleic acid strand. Generally, the synthesis will be initiated at the 3' end of each primer and will proceed in the 5' direction along the template strand, until synthesis terminates, producing molecules of different lengths.

The thermostable enzyme herein must satisfy a single criterion to be effective for the amplication reaction, i.e., the enzyme must not become irreversibly denatured (inactivated) when subjected to the elevated temperatures for the time necessary to effect denaturation of double-stranded nucleic acids. Irreversible denaturation for purposes herein refers to permanent and complete loss of enzymatic activity. The heating conditions necessary for denaturation will depend, e.g., on the buffer salt concentration and the length and nucleotide composition of the nucleic acids being denatured, but typically range from about 90 to about 96° C. for a time depending mainly on the temperature and the nucleic acid length, typically about 0.5 to four minutes. Higher temperatures may be tolerated as the buffer salt concentration and/or GC composition of the nucleic acid is increased. Preferably, the enzyme will not become irreversibly denatured at about 90–100° C.

The thermostable enzyme herein preferably has an optimum temperature at which it functions that is higher than about 40° C., which is the temperature below which hybridization of primer to template is promoted, although, depending on (1) magnesium and salt, concentrations and (2) composition and length of primer, hybridization can occur at higher temperature (e.g., 45–70° C.). The higher the temperature optimum for the enzyme, the greater the specificity and/or selectivity of the primer-directed extension process. However, enzymes that are active below 40° C., e.g., at 37° C., are also with the scope of this invention provided they are heat-stable. Preferably, the optimum temperature ranges from about 50° to 90° C., more preferably 60–80° C.

Amino Acid Residue: The amino acid residues described herein are preferred to be in the "L" isomeric form. However, residues in the "D" isomeric form can be substituted for any L-amino acid residue, as long as the desired functional property is retained by the polypeptide. NH2 refers to the free amino group present at the amino- or carboxy-terminus of a polypeptide. COOH refers to the free carboxy group present at the carboxy terminus of a polypeptide. The amino-terminal $NH_2$ group and carboxy-terminal COOH group of free polypeptides are typically not set forth in a formula. A hyphen at the amino- or carboxy-terminus of a sequence indicates the presence of a further sequence of amino acid residues or a respective $NH_2$ or COOH terminal group. In keeping with standard polypeptide nomenclature, *J. Biol. Chem.*, 243:3552–59 (1969) and adopted at 37 CFR §1.822(b)(2), abbreviations for amino acid residues are shown in the following Table of Correspondence:

TABLE OF CORRESPONDENCE

| SYMBOL | | |
|---|---|---|
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |

-continued

TABLE OF CORRESPONDENCE

| SYMBOL | | |
|---|---|---|
| 1-Letter | 3-Letter | AMINO ACID |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

It should be noted that all amino acid residue sequences are represented herein by formulae whose left and right orientation is in the conventional direction of amino-terminus to carboxy-terminus.

Nucleotide: a monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. When the nucleoside contains a phosphate group bonded to the 3' or 5' position of the pentose it is referred to as a nucleotide. A sequence of operatively linked nucleotides is typically referred to herein as a "base sequence" or "nucleotide sequence", and is represented herein by a formula whose left to right orientation is in the conventional direction of 5'-terminus to 3'-terminus.

Base Pair (bp): A partnership of adenine (A) with thymine (T), or of cytosine (C) with guanine (G) in a double stranded DNA molecule.

B. Pfu DNA Polymerase I (Pyro Polymerase)

Pyro polymerase, the thermostable DNA polymerase of the present invention, can be obtained from any source and can be a native or recombinant protein. A preferred Pyro polymerase is isolated from *Pyrococcus furiosus*. *P. furiosus* is available from Dentsche Sammlung Von Microorganismen (DSM), Grise-Bach StraSSE 8, d-3400 Göttengen, FRG, under the accession number DSM-6217.

For isolating the native protein from *P. furiosus* cells, such cells are grown using any suitable technique. A variety of such techniques have been reported, those preferred being described by Fiala et al., *Arch. Microbiol*, (1986) 145:56–61, and Bryant et al., *J. Biol. Chem.*, (1989) 264:5070–5079, the disclosures of which are incorporated herein by reference.

After cell growth, the isolation and purification of Pyro polymerase takes place in about 3 stages, each of which is performed at, and preferably below, room temperature, preferably about 4° C.

In the first step, the cells are concentrated from the growth medium, typically by centrifugation or filtration.

In the second step, the cells are lysed and the supernatant is segregated and recovered from the cellular debris. Lysis is typically accomplished by mechanically applying sheer stress and/or enzymatic digestion. Segregation of the supernatant is usually accomplished by centrifugation.

The third step removes nucleic acids and some protein. The supernatant from the second step is applied to an agarose resin strong anionic exchange column, such as Q-sepharose from Pharmacia (Piscataway, N.J.) equilibriated with column buffer [50 mM tris-hydroxymethylaminomethane (Tris), pH 8.2, 10 mM beta mercaphroethanol, and 1 mM ethylenediaminetetraacetic acid (EDTA)]. The supernatant is washed through the column with the column buffer and the pass-through and washes are collected and centrifuged to remove any insoluble material. The supernatant is segregated, usually dialyzed, and then recovered to form a fraction containing partially purified Pyro polymerase.

The fourth step removes substantially all (90%) of the remaining contaminating proteins and comprises applying the fraction recovered from step three to a phosphocellulose column equilibrated with the before described column buffer. The column is washed with the column buffer until the optical density of the wash eluate is at the buffer baseline at 280 nm. The immobilized Pyro polymerase is thereafter eluted with a linear salt gradient comprising O M to about 0.7 M salt dissolved in the column buffer, the salt being NaCl, KCl, and the like. Protein eluted from the column at about 200 mM salt typically contains the highest concentrations of assayable Pyro polymerase.

In preferred embodiments, the Pyro polymerase preparation obtained from the fourth step is further purified in a fifth step by FPLC chromatography through a high performance cation exchange column, such as the Mono S column available from Pharmacia, Piscataway, N.J., equilbriated with the before described column buffer. After application, the column is washed to remove non-bound contaminants. The immobilized Pyro polymerase is then eluted with the before-described linear salt gradient at about 120 nM salt concentration. The Pyro polymerase eluate is then typically dialysed against the column buffer to remove excess salt. A stabilizing agent, such as glycerol, can be added to the preparation at this time to facilitate low temperature storage. Typically, the fraction is again dialyzed against a low salt buffer, e.g., 50 mM Tris pH 7.5, 1 mM dithiothreitol, 0.1 mM EDTA, 0.1% Tween 20, and 0.1% non-idet P40.

In further preferred embodiments the Pyro polymerase preparation of step five is applied to a crosslinked agarose affinity column, such as the Affi-Gel Blue column available from BioRad, Richmond, Calif., equilibrated with the before-described column buffer. Non-bound protein is washed from the column and the Pyro polymerase is eluted with the before-described salt gradient with the Pyro polymerase typically being recovered at about 280 mM salt concentration. Thereafter, the Pyro polymerase preparation is usually concentrated about 5–10 fold and dialysed against column buffer. Typically, a stabilizing agent, such as glycerol, is added to the preparation to facilitate low temperature storage.

The amino-terminal amino acid residue sequence of Pyro polymerase can be determined by any suitable method, such as by automated Edman degradation, and the like. The amino acid residue sequence of a preferred Pyro polymerase is shown in SEQ ID NO 1 from residue 1 to 775.

The molecular weight of the dialyzed product may be determined by any technique, for example, by sodium dodecylsulfate-polyacrylamide gel electrophoresis (SDS-PAGE) using protein molecular weight markers. Native Pyro polymerase purified by the above method has a relative molecular weight, determined by SDS-PAGE under non-reducing conditions, of about 90,000–93,000 daltons.

In preferred embodiments, Pyro polymerase is used in combination with a thermostable buffering agent such as TAPS (N-tris[Hydroxymethyl]methyl-3-aminopropanesulfonic acid; ([2-Hydroxy-1, 1 -bis(hydroxy-methyl)-ethyl] amino-1-propanesulfonic acid), available from Sigma, St. Louis, Mo. (Catalog P7905).

C. Recombinant Pyro Polymerase

Pyro polymerase can also be produced by recombinant DNA (rDNA) techniques, as the gene encoding the enzyme can be cloned from *P. furiosus* genomic DNA. Thus, the present invention also contemplates a DNA segment consisting essentially of a sequence of nucleotide base sequence encoding a Pyro polymerase of this invention. An exemplary DNA sequence, obtained from the native gene, coding for a preferred Pfu I protein is shown in SEQ ID NO 2 from nucleotide base 224 to base 2548, which spans the coding portion of SEQ ID NO 2.

The isolated gene can be operably linked to an expression system to form an rDNA capable of expressing, in a compatible host, Pyro polymerase.

Of course, modifications to the primary structure itself by deletion, addition, or alteration of the amino acids incorporated into the protein sequence during translation can be made without destroying the activity of the protein. Such substitutions or other alterations result in proteins having an amino acid sequence encoded by DNA falling within the contemplated scope of the present invention.

1. Cloning and Expression of the Pyro Polymerase Gene

Polyclonal antiserum from rabbits immunized with the purified 90,000–93,000 dalton polymerase of this invention can be used to probe a *P. furiosus* partial genomic expression library to obtain the appropriate coding sequence as described below. The cloned genomic sequence can be expressed as a fusion protein, expressed directly using its own control sequences, or expressed by constructions using control sequences appropriate to the particular host used for expression of the enzyme.

Thus, the complete coding sequence for Pyro polymerase from which expression vectors applicable to a variety of host systems can be constructed and the coding sequence expressed. It is also evident from the foregoing that portions of the Pyro polymerase-encoding sequence are useful as probes to retrieve other similar thermostable polymerase-encoding sequences in a variety of Archaebacteria species, particularly from other *Pyrococcus* species and *P. furiosus* strains. Accordingly, portions of the genomic DNA encoding at least six contiguous amino acids can be synthesized and used as probes to retrieve additional DNAs encoding an Archaebacteria thermostable polymerase. Because there may not be a precisely exact match between the nucleotide sequence in the *P. furiosus* form described herein and that in the corresponding portion of other species or strain, oligomers containing approximately 18 nucleotides (encoding the six amino acid stretch) are probably necessary to obtain hybridization under conditions of sufficient stringency to eliminate false positives. The sequences encoding six amino acids would supply information sufficient for such probes.

Exemplary degenerate Pfu DNA polymerase I gene probes are shown in Table 1.

TABLE 1

Degenerate Pfu DNA Polymerase I Gene Probes[1]

```
                              A
                    T  T  T   I
         1)      5'GACTACATCACCGAIGAIGG3'

T  T      A  A
         2)      5'CCCTCCTCIGTIATGTAGTC3'

T     A  A  T
```

TABLE 1-continued

Degenerate Pfu DNA Polymerase I Gene Probes[1]

```
                              A T T A
3)         5'TTCAAGAAGAACGG-3'

A T T A
4)         5'CCGTTCTTCTTGAA-3'
```

[1]Nucleotide sequence degenerate substitutions are bases directly above the positions in the sequence where the substitutions were made. In some cases, degeneracy was accomplished by substituting inosine (I) in the sequence.

A preferred and exemplary cloning protocol for isolation of a pfu pol I gene is described in the Examples. From the clone pF72 described in the Examples, the nucleotide sequence of a preferred gene encoding pfu pol I was described and is shown in SEQ ID NO 2, and can be utilized for the production of recombinant Pyro polymerase.

In general terms, the production of a recombinant form of Pyro polymerase typically involves the following:

First, a DNA is obtained that encodes the mature (used here to include all muteins) enzyme or a fusion of the Pyro polymerase either to an additional sequence that does not destroy its activity, or to an additional sequence cleavable under controlled conditions (such as treatment with peptidase) to give an active protein. If the sequence is uninterrupted by introns it is suitable for expression in any host. This sequence should be in an excisable and recoverable form.

The excised or recovered coding sequence is then preferably placed in operable linkage with suitable control sequences in a replicable expression vector. The vector is used to transform a suitable host and the transformed host cultured under favorable conditions to effect the production of the recombinant Pyro polymerase. Optionally the Pyro polymerase is isolated from the medium or from the cells; recovery and purification of the protein may not be necessary in some instances, where some impurities may be tolerated.

Each of the foregoing steps can be done in a variety of ways. For example, the desired coding sequences may be obtained from genomic fragments and used directly in appropriate hosts. The constructions for expression vectors operable in a variety of hosts are made using appropriate replicons and control sequences, as set forth below. Suitable restriction sites can, if not normally available, be added to the ends of the coding sequence so as to provide an excisable gene to insert into these vectors.

The control sequences, expression vectors, and transformation methods are dependent on the type of host cell used to express the gene. Generally, procaryotic, yeast, insect or mammalian cells are presently useful as hosts. Procaryotic hosts are in general the most efficient and convenient for the production of recombinant proteins and therefore are preferred for the expression of Pyro polymerase.

2. Control Sequences and Corresponding Hosts

Procaryotes most frequently are represented by various strains of *E. coli*. However, other microbial strains may also be used, such as bacilli, for example, *Bacillus subtillis*, various species of *Pseudomonas*, or other bacterial strains. In such procaryotic systems, plasmid vectors that contain replication sites and control sequences derived from species compatible with the host are used. For example, *E. coli* is typically transformed using derivatives of pBR322, a plasmid derived from an *E. coli* species by Bolivar, et al., *Gene*, (1977) 2:95 and Sutcliffe, *Nuc. Acids Res.*, (1978) 5:2721–28. pBR322 contains genes for ampicillin and tetracycline resistance, and thus provides additional markers that can be either retained or destroyed in constructing the desired vector. Commonly used procaryotic control sequences, which are defined herein to include promoters for transcription initiation, optionally with an operator, along with ribosome binding site sequences, include such commonly used promoters as the B-lactamase (penicillinase) and lactose (lac) promoter systems (Chang, et al., *Nature*, (1977) 198:1056), the tryptophan (trp) promoter system (Goeddel, et al., *Nucleic Acids Res.*, (1980) 8:4057) and the lambda-derived $P_L$ promoter (Shimatake, et al., *Nature*, (1981) 292:128) and N-gene ribosome binding site, which has been made useful as a portable control cassette (as set forth in U.S. Pat. No. 4,711,845), which comprises a first DNA sequence that is the $P_L$ promoter operably linked to a stream of a third DNA sequence having at least one restriction site that permits cleavage with six bp 3' of the $N_{RBS}$ sequence. Also useful is the phosphatase A (phoA) system described by Change, et al. in European Patent Publication No. 196,864. However, any available promoter system compatible with procaryotes can be used. Typical bacterial plasmids are pUCS, pUC9, pBR322 and pBR329 available from Bio-Rad Laboratories, (Richmond, Calif.) and pPL and pkk233-2, available from Pharmacia (Piscataway, N.J.) or Clone Tech (Palo Alto, Calif.).

In addition to bacteria, eucaryotic microbes, such as yeast, may also be used as hosts. Laboratory strains of *Saccharomyces cerevisiae*, Baker's yeast, are most used, although a number of other strains are commonly available. While vectors employing the 2 micron origin of replication are illustrated (Broach, J. R., *Meth. Enz.*, (1983) 101:307), other plasmid vectors suitable for yeast expression are known (see, for example, Stinchcomb, et al., *Nature*, (1979) 282:39, Tschempe, et al., *Gene*, (1980) 10:157, Clarke, L., et al., *Meth. Enz* (1983) 101:300), Brake et al., *Proc. Natl. Acad. Sci, USA*, (1984) 81:4642–4647, and Halewell et al., *Biotechnology*, (1987) 5:363–366. Control sequences for yeast vectors include promoters for the synthesis of glycolytic enzymes (Hess, et al., *J. Adv. Enzyme Reg.*, (1968) 7:149; Holland, et al., *Biotechnology* (1978) 17:4900).

Additional promoters known in the art include the promoter for 3-phosphoglycerate kinase (Hitzeman, et al., *J. Biol. Chem.*, (1980) 255:2073) and those for other glycolytic enzymes, such as glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other promoters that have the additional advantage of transcription controlled by growth conditions are the promoter regions for alcohol dehydrogenase 2, iscoytochrome C, acid phosphatase, degradative enzymes associated with nitrogen metabolism, and enzymes responsible for maltose and galactose utilization (Holland, supra).

It is also believed that terminator sequences are desirable at the 3' end of the coding sequences. Such terminators are found in the 3' untranslated region following the coding sequences in yeast-derived genes. Many of the vectors illustrated contain control sequences derived from the enolase gene containing plasmid peno46 (Holland, M. M., et al., *J. Biol. Chem.*, (1981) 256:1385) or the LEU2 gene obtained from YEp13 (Broach, J., et al., *Gene*, (1978) 8:21); however, any vector containing a yeast-compatible promoter, origin of replication, and other control sequences is suitable.

It is also, of course, possible to express genes encoding polypeptides in eucaryotic host cell cultures derived from multicellular organisms. See, for example, *Tissue Culture*, Academic Press, Cruz and Patterson, editors (1973). Useful host cell lines include murine myelomas N51, VERO and HeLA cells, and Chinese hamster ovary (CHO) cells available from the ATCC as CCL61, and NIH/3T3 mouse cells available from the ATCC as CRL1658. Expression vectors for such cells ordinarily include promoters and control sequences compatible with mammalian cells such as, for example, the commonly used early and late promoters from Simian Virus 40 (SV 40) (Fiers, et al., *Nature*, (1978) 273:113), or other viral promoters such as those derived from polyoma, Adenovirus 2, bovine papilloma virus, or avian sarcoma viruses, or immunoglobulin promoters and heat shock promoters. A system for expressing DNA in mammalian systems using the BPV as a vector is disclosed in U.S. Pat. No. 4,419,446. A modification of this system is described in U.S. Pat. No. 4,601,978. General aspects of mammalian cell host system transformations have been described in U.S. Pat. No. 4,399,216. It now appears, also, that "enhancer" regions are important in optimizing expression; these are, generally, sequences found upstream of the promoter region. Origins of replication may be obtained, if needed, from viral sources. However, integration into the chromosome is a common mechanism for DNA replication in eucaryotes.

Plant cells are also now available as hosts, and control sequences compatible with plant cells such as the nopaline synthase promoter and polyadenylation signal sequences (Depicker, A., et al., *J. Mol. Appl. Gen.*, (1982) 1:561) are available. See, also, U.S. Pat. No. 4,962,028, U.S. Pat. No. 4,956,282, U.S. Pat. No. 4,886,753 and U.S. Pat. No. 4,801,540.

Recently, in addition, expression systems employing insect cells utilizing the control systems provided by baculovirus vectors have been described (Miller, D. W., et al., in *Genetic Engineering* (1986) Setlow, J. K. et al., eds., Plenum Publishing, Vol. 8, pp. 277–297). See, also, U.S. Pat. No. 4,745,051 and No. 4,879,236. These systems are also successful in producing Pyro polymerase.

A preferred DNA segment containing both the pfu pol I coding portion and control sequences at the 5' and 3' termini of the coding portion is shown in SEQ ID NO 2 from nucleotide base 1 to base 3499.

3. Transformations

The recombinant DNA molecules of the present invention are introduced into host cells, via a procedure commonly known as transformation or transfection. Transformation of appropriate host cells with a recombinant DNA molecule of the present invention is accomplished by well known methods that typically depend on the type of vector used. With regard to transformation of procaryotic host cells or other cells that contain substantial cell wall barriers, see, for example, Cohen et al., *Proc. Natl. Acad. Sci. USA*, 69:2110 (1972); and Maniatis et al., *Molecular Cloning. A Laboratory Manual*, Cold Spring Harbor Laboratory, Cold Spring Harbor, N.Y. (1982). With regard to transformation of vertebrate cells with retroviral vectors containing rDNA, see, for example, Sorge et al., *Mol. Cell. Biol.*, 4:1730–37 (1984); and Wigler et al., *Proc. Natl. Acad. Sci. USA*, 76:1373–76 (1979).

Infection with *Agrobacterium tumefaciens* (Shaw, C. H., et al., *Gene*, (1983) 23:315) is used for certain plant cells. For mammalian cells without cell walls, the calcium phosphate precipitation method of Graham and van der Eb, *Virology* (1978) 52:546 is preferred. Transformations into yeast are carried out according to the method of Van Solingen, P., et al., *J. Bact.* (1977) 130:946 and Hsiao, C. L., et al., *Proc. Natl. Acad. Sci.* (*USA*), (1979) 76:3829.

Successfully transformed cells, i.e., cells that contain a recombinant DNA (rDNA) molecule of the present invention, are usually monitored by an appropriate immunological, hybridization or functional assay. For example, cells resulting from the introduction of an rDNA of the present invention can be cloned to produce monoclonal colonies. Cells from those colonies can be harvested, lysed and their DNA content examined for the presence of the rDNA using a method such as that described by Southern, *J. Mol. Biol.*, 98:503 (1975) or Berent et al., *Biotech.*, 3:208 (1985).

In addition to directly assaying for the presence of rDNA, successful transformation can be confirmed by well known immunological methods when the rDNA is capable of directing the expression of Pyro polymerase. For example, cells successfully transformed with a subject rDNA containing an expression vector produce a polypeptide displaying a characteristic antigenicity. Samples of a culture containing cells suspected of being transformed are harvested and assayed for a subject polypeptide (Pyro polymerase) using antibodies specific for that polypeptide antigen, such as those produced by an appropriate hybridoma.

A particularly convenient assay technique involves fusing the Pyro polymerase-encoding DNA to a Lac Z gene in a suitable plasmid, e.g. pLG. Since the plasmid lacks a promoter and Shine-Dalgarno sequence, no β-galactosidase is synthesized. However, when a portable promoter fragment is properly positioned in front of the fused gene, high levels of a fusion protein having β-galactosidase activity should be expressed. The plasmids are used to transform Lac-bacteria which are scored for β-galactosidase activity on lactose indicator plates. Plasmids having optimally placed promoter fragments are thereby recognized. These plasmids can then be used to reconstitute the fusion protein gene which is expressed at high levels.

Thus, in addition to the transformed host cells themselves, cultures of the cells are contemplated as within the present invention. The cultures include monoclonal (clonally homogeneous) cultures, or cultures derived from a monoclonal culture, in a nutrient medium. Nutrient media useful for culturing transformed host cells are well known in the art and can be obtained from several commercial sources. In embodiments wherein the host cell is mammalian, a "serum-free" medium is preferably used.

The present method entails culturing a nutrient medium containing host cells transformed with a recombinant DNA molecule of the present invention that is capable of expressing a gene encoding a subject polypeptide. The culture is maintained for a time period sufficient for the transformed cells to express the subject polypeptide. The expressed polypeptide is then recovered from the culture.

Once a gene has been expressed in high levels, a DNA fragment containing the entire expression assembly, e.g., promoter, ribosome-binding site, and fusion protein gene) may be transferred to a plasmid that can attain very high copy numbers. For instance, the temperature-inducible "runaway replication" vector pKN402 may be used. Preferably, the plasmid selected will have additional cloning sites which allow one to score for insertion of the gene assembly. See, Bittner et al. *Gene*, 15:31 (1981). Bacterial cultures transformed with the plasmids are grown for a few hours to increase plasmid copy number, e.g., to more than 1000 copies per cell. Induction may be performed in some cases by elevated temperature and in other cases by addition of an

4. Construction of a Lambda Expression Library

The strategy for isolating DNA encoding desired proteins such as the Pyro polymerase encoding DNA, using the bacteriophage vector lambda gt11, is as follows. A library can be constructed of EcoRI-flanked AluI fragments, generated by complete digestion of *P. furiosus* DNA, inserted at the EcoRI site in the lambda gt11 phage (Young and Davis, *Proc. Natl. Acad. Sci.* (*USA*), (1983) 80:1194–1198). Because the unique EcoRI site in this bacteriophage is located in the carboxyl-terminus of the B-galactosidase gene, inserted DNA (in the appropriate frame and orientation) is expressed as protein fused with B-galactosidase under the control of the lactose operon prompter/operator.

Genomic expression libraries are then screened using the antibody plaque hybridization procedure. A modification of this procedure, referred to as "epitope selection," uses antiserum against the fusion protein sequence encoded by the phage, to confirm the identification of hybridized plaques. Thus, this library of recombinant phages could be screened with antibodies that recognize the 90,000–93,000 dalton Pyro polymerase in order to identify phage that carry DNA segments encoding the antigenic determinants of the Pyro polymerase protein.

Approximately $2 \times 10^5$ recombinant phage are screened using rabbit Pyro polymerase antiserum. In this primary screen, positive signals are detected and one or more of these plaques are purified from candidate plaques which failed to react with preimmune serum and reacted with immune serum and analyzed in some detail. Anti-Pyro polymerase antibodies can be prepared by a number of known methods, see, for example, U.S. Pat. No. 4,082,735, U.S. Pat. No. 4,082,736, and U.S. Pat. No. 4,493,795.

To examine fusion proteins produced by the recombinant phage, lysogens of the phage in the host Y1089 are produced. Upon induction of the lysogens and gel electrophoresis of the resulting proteins, each lysogen may be observed to produce a new protein, not found in other lysogens, or duplicate sequences may result. Phage containing positive signals are picked. Typically, one positive plaque is picked for further identification and replated at lower densities to purify recombinants and the purified clones are analyzed by size class via digestion with EcoRI restriction enzyme. Probes can then be made of the isolated DNA insert sequences and labeled appropriately and these probes can be used in conventional colony or plaque hybridization assays described in Maniatis et al., *Molecular Cloning: A Laboratory Manual*, (1982), the disclosure of which is incorporated herein by reference. Particular hybridization conditions that may be used include incubating DNA at 42° C. in a hybridization buffer comprising 0.9 M NaCl and 50% formamide. Wash conditions that may be used after hybridization include incubating DNA at 68° C. in a wash buffer comprising 0.015 M NaCl and 0.5% sodium dodecyl sulfate.

5. Recombinant DNA Molecules

The present invention further contemplates a recombinant DNA (rDNA) that includes a Pyro polymerase-encoding DNA segment of the present invention operatively linked to a vector for replication and/or expression. Preferred rDNA molecules contain less than 50,000 nucleotide base pairs, usually less than 20,000 base pairs and preferably less than about 10,000 base pairs. Preferably, a Pyro polymerase-encoding DNA of this invention is in the form of a plasmid, cosmid or phage.

A preferred rDNA molecule includes a nucleotide sequence shown in SEQ ID NO 2 from nucleotide base 224 to base 2548.

A rDNA molecule of the present invention can be produced by operatively linking a vector to a DNA segment of the present invention.

As used herein, the term "vector" refers to a nucleic acid molecule capable of transporting between different genetic environments another nucleic acid to which it has been operatively linked Preferred vectors are those capable of autonomous replication and/or expression of nucleic acids to which they are operatively linked are referred to herein as "expression vectors". As used herein, the term "operatively linked", in reference to DNA segments, describes that the nucleotide sequence is joined to the vector so that the sequence is under the transcriptional and translation control of the expression vector and can be expressed in a suitable host cell.

As is well known in the art, the choice of vector to which a protein encoding DNA segment of the present invention is operatively linked depends upon the functional properties desired, e.g., protein expression, and upon the host cell to be transformed. These limitations are inherent in the art of constructing recombinant DNA molecules. However, a vector contemplated by the present invention is at least capable of directing the replication, and preferably also expression, of a gene operatively linked to the vector.

In preferred embodiments, a vector contemplated by the present invention includes a procaryotic replicon, i.e., a DNA sequence having the ability to direct autonomous replication and maintenance of the recombinant DNA molecule extrachromosomally in a procaryotic host cell, such as a bacterial host cell, transformed therewith. Such replicons are well known in the art. In addition, those embodiments that include a procaryotic replicon may also include a gene whose expression confers a selective advantage such as amino acid nutrient dependency or drug resistance to a bacterial host transformed therewith as is well known, in order to allow selection of transformed clones. Typical bacterial drug resistance genes are those that confer resistance to ampicillin, tetracycline, or kanamycin.

Those vectors that include a procaryotic replicon may also include a procaryotic promoter capable of directing the expression (transcription and translation) of the gene transformed therewith. A promoter is an expression control element formed by a DNA sequence that permits binding of RNA polymerase and transcription to occur. Promoter sequences compatible with bacterial hosts are typically provided in plasmid vectors containing convenient restriction sites for insertion of a DNA segment of the present invention. Bacterial expression systems, and choice and use of vectors in those systems is described in detail in "Gene Expression Technology", *Meth. Enzymol.*, Vol 185, Goeddel, Ed., Academic Press, NY (1990).

Expression vectors compatible with eucaryotic cells, preferably those compatible with vertebrate cells, can also be used to form the recombinant DNA molecules of the present invention. Eucaryotic cell expression vectors are well known in the art and are available from several commercial sources. Typically, such vectors are provided containing convenient restriction sites for insertion of the desired gene. Typical of such vectors are pSVL and pKSV-10 (Pharmacia), pBPV-1/pML2d (International Biotechnologies, Inc.), and pTDT1 (ATCC, #31255).

In preferred embodiments, the eucaryotic cell expression vectors used to construct the recombinant DNA molecules of the present invention include a selectable phenotypic marker that is effective in a eucaryotic cell, such as a drug resistance selection marker or selective marker based on nutrient dependency. A preferred drug resistance marker is the gene whose expression results in neomycin resistance, i.e., the neomycin phosphotransferase (neo) gene. Southern et al., *J. Mol. Appl. Genet.*, 1:327–341 (1982).

The use of retroviral expression vectors to form the rDNAs of the present invention is also contemplated. As used herein, the term "retroviral expression vector" refers to a DNA molecule that includes a promoter sequence derived from the long terminal repeat (LTR) region of a retrovirus genome.

In addition to using strong promoter sequences to generate large quantities of mRNA coding for the expressed fusion proteins of the present invention, it is desirable to provide ribosome-binding sites in the mRNA to ensure efficient translation. The ribosome-binding site in *E. coli* includes an initiation codon (AUG) and a sequence 3–9 nucleotides long located 3–11 nucleotides upstream from the initiation codon (the Shine-Dalgarno sequence). See, Shine et al., *Nature*, 254:34 (1975). Methods for including a ribosome-binding site in mRNAs corresponding to the expressed proteins are described by Maniatis, et al. *Molecular Cloning: A Laboratory Manual*, Cold Spring Harbor Laboratory Press, NY pp. 412–417 (1982). Ribosome binding sites can be modified to produce optimum configuration relative to the structural gene for maximal expression of the structural gene. Halewell et al., *Nucl. Acid. Res.*, (1985) 13:2017–2034.

Construction of suitable vectors containing the desired coding and control sequences employs standard ligation and restriction techniques that are well understood in the art. Isolated plasmids, DNA sequences, or synthesized oligonucleotides are cleaved, tailored, and religated in the form desired.

Site-specific DNA cleavage is performed by treating with the suitable restriction enzyme (or enzymes) under conditions that are generally understood in the art, and the particulars of which are specified by the manufacturer of these commercially available restriction enzymes. See e.g., New England Biolabs, Product Catalog. In general, complete digestion is obtained by admixing about 1 ug of plasmid or DNA sequence with one unit of enzyme in about 20 ml of buffer solution. Incubation times of about one hour to two hours at about 37° C. are workable, although variations can be tolerated. After each incubation, protein is removed by extraction with phenol/chloroform, and may be followed by ether extraction, and the nucleic acid recovered from aqueous fractions by precipitation with ethanol. If desired, size separations is found in Methods in Enzymology (1980) 65:499–560.

Restriction-cleaved fragments may be blunt-ended by treating with large fragment *E. coli* DNA polymerase I (Klenow) in the presence of the four deoxynucleotide triphosphates (dNTPs) using incubation times of about 15 to 25 minutes at 20 to 25° C. in 50 mM Tris pH 7.6, 50 mM NaCl, 10 mM MgCl$_2$, 10 mM DTT and 50–100 µM dNTPs. The Klenow fragment fills in at 5' sticky ends, but chews back protruding 3' single strands even though the four dNTPs are present. If desired, selective repair can be performed by supplying only one of the, or selected, dNTPs within the limitations dictated by the nature of the sticky ends. After treatment with Klenow, the mixture is extracted with phenol/chloroform and ethanol precipitated. Treatment under appropriate conditions with S1 nuclease results in hydrolysis of any single-stranded portion.

Synthetic oligonucleotides may be prepared using the triester method of Matteucci, et al., (*J. Am. Chem. Soc.*, (1981) 103:3185–3191) or using automated synthesis methods. Kinasing of single strands prior to annealing or for labeling is achieved using an excess, e.g., approximately 10 units of polynucleotide kinase to 1 nM substrate in the presence of 50 mM Tris, pH 7.6, 10 mN MgCl$_2$, 5 mM dithiothreitol, 1–2 mM ATP. If kinasing is for labeling of probe, the ATP will contain high specific activity $^{32}$P.

Ligations are performed in 15–30 µl volumes under the following standard conditions and temperatures: 20 mM Tris-Cl pH 7.5, 10 mM MgCl$_2$, 10 mM DTT, 33 µg/ml BSA, 10 mM-50 mM NaCl, and either 40 µM ATP, 0.01–0.02 (Weiss) units TA DNA ligase at 0° C. (for "sticky end" ligation) or 1 mM ATP, 0.3–0.6 (Weiss) units T4 DNA ligase at 14° C. (for "blunt end" ligation). Intermolecular "sticky end" ligations are usually performed at 33–100 µg/ml total DNA concentrations (5–100 nM total end concentration). Intermolecular blunt end ligations (usually employing a 10–30 fold molar excess of linkers) are performed at 1 µM total ends concentration.

In vector construction employing "vector fragments", the vector fragment is commonly treated with bacterial alkaline phosphatase (BAP) in order to remove the 5' phosphate and prevent religation of the vector. BAP digestions are conducted at PH 8 in approximately 150 mM Tris, in the presence of Na$^+$ and Mg$^{+2}$ using about 1 unit of BAP per mg of vector at 60° C. for about one hour. In order to recover the nucleic acid fragments, the preparation is extracted with phenol/chloroform and ethanol precipitated. Alternatively, religation can be prevented in vectors that have been double digested by additional restriction enzyme digestion of the unwanted fragments.

For portions of vectors derived from cDNA or genomic DNA that require sequence modifications, sit-specific primer-directed mutagenesis is used. this technique is now standard in the art, and is conducted using a primer synthetic oligonucleotide complementary to a single-stranded phage DNA to be mutagenized except for limited mismatching, representing the desired mutation. Briefly, the synthetic oligonucleotide is used as a primer to direct synthesis of a strand complementary to the phage, and the resulting double-stranded DNA is transformed into a phage-supporting host bacterium. Cultures of the transformed bacteria are plated in top agar, permitting plaque formation from single cells that harbor the phage.

Theoretically, 50% of the new plaques will contain the phage having, as a single strand, the mutated form; 50% will have the original sequence. The plaques are transferred to nitrocellulose filters and the "lifts" hybridized with kinased synthetic primer at a temperature that permits hybridization of an exact match, but at which the mismatches with the original strand are sufficient to prevent hybridization. Plaques that hybridize with the probe are then picked and cultured, and the DNA is recovered.

6. Verification of Construction

Correct ligations for plasmid construction are confirmed by first transforming *E. coli* strain MM294, or other suitable host, with the ligation mixture. Successful transformants are selected by ampicillin, tetracycline or other antibiotic resistance or using other markers, depending on the mode of plasmid construction, as is understood in the art. Plasmids from the transformants are then prepared according to the method of Clewell, D. B., et al., *Proc. Natl. Acad. Sci. (USA)*, (1969) 62:1159, optionally following chloramphenicol amplication (Clewell, D. B., *J. Bacteriol.*, (1972), 110: 667). The isolated DNA is analyzed by restriction digest mapping and/or sequenced by the dideoxy method of Sanger, F., et al., *Proc. Natl. Acad. Sci. (USA)*, (1977) 74:5463 as further described by Messing, et al., *Nucleic Acids Res.*, (1981) 9:309, or by the method of Maxam, et al., *Methods in Enzymology*, (1980) 65:499.

Host strains useful in cloning and expression are as follows:

For cloning and sequencing, and for expression of constructions under control of most bacterial promoters, *E. coli* strain MM294 obtained from *E. coli* Genetic Stock Center GCSC #6135, is particularly useful. For expression under control of the $P_L N_{RBS}$ promoter, *E. coli* strain K12 MC1000 lambda lysogen, $N_7 N_{53c} I857$ $SusP_{80}$ (ATCC 39531), may be used. Also useful is *E. coli* DG116, (ATCC 53606).

For M13 phage recombinants, *E. coli* strains susceptible to phage infection, such as *E. coli* K12 strain DG98, are employed. The DG98 strain has been deposited with ATCC Jul. 13, 1984 and has accession number 39768.

The thermostable enzyme of this invention may be used for any purpose in which such enzyme is necessary or desirable. In a particularly preferred embodiment, the enzyme herein is employed in the amplification protocol set forth below.

EXAMPLES

The following examples are intended to illustrate, but not limit, the present invention.

1. Culturing of *Pyrococcus furiosus* and Preparation of Pf Cell Paste

The following describes how the hyperthermophilic archaebacterium, *P. furiosus*, is routinely grown in a 500 liter fermentor for the purpose of obtaining cell mass in sufficient quantities for large scale protein purification. It is a modified version (Bryant et al., *J. Biol. Chem.*, 264: 5070–5079 (1989)) of the original protocol of Fiala et al., *Arch. Microbiol.*, 145:56–61 (1986).

For culture maintenance, *P. furiosus* (DSM 3638) is routinely grown at 85–88° C. as a closed static culture in 100 ml of the medium described in Table 2.

TABLE 2

| | |
|---|---|
| Maltose | 5 g/l |
| NH$_4$Cl | 1.25 g/l |
| Elemental Sulfur | 5 g/l |
| Na$_2$S | 0.5 g/l |
| Synthetic Sea Water[1] | |
| Vitamin mixture[2] | 1 ml/l |
| FeCl$_3$ | 25 µM |
| Na$_2$WO$_4$ | 10 µM |
| Yeast Extract | 0.01% |

[1]Synthetic Sea Water:
NaCl, 13.8 g/l
MgSO$_4$, 3.5 g/l
MgCl$_2$, 2.7 g/l
KCl, 0.3 g/l
CaCl$_2$, 0.75 g/l
KH$_2$PO$_4$, 0.5 g/l
NaBr, 0.0–5 g/l
KI, 0.05 g/l
H$_3$BO$_3$, 0.015 g/l
Sodium citrate, 0.005 g/l
[2]Vitamin mixture [Balch et al., Microbiol. Rev., 43:260–296 (1979)]:
Biotin, 2 mg/l
Folic acid, 2 mg/l
Pyridoxine hydrochloride, 10 mg/l
Thiamine hydrochloride, 5 mg/l
Riboflavin, 5 mg/l
Nicotinic acid, 5 mg/l
DL-Calcium pantothenate, 5 mg/l
Vitamin B$_{12}$, 0.1 mg/l
p-Aminobenzoic acid, 5 mg/l
Lipoic acid, 5 mg/l Growth is monitored by the increase in turbidity at 600 nm. Cells can be stored in the same medium at 4° C. and remain viable for at least a year, although periodic transfer is recommended.

Large scale (preparative) growth of *P. furiosus* was performed as follows:

Growth medium according to Table 1, was prepared, except that the sulfide was replaced with titanium (III) nitrilotriacetate (final concentration, 30 µM as described in Moench et al., *J. Microbiol. Meth.*, 1:199–202 (1983)] and the elemental sulfur is omitted. The medium was then sparged with Argon (Ar).

A two liter flask was inoculated with two 100 ml cultures. The two liter culture was used as an inoculum for a 20 liter culture. Two 20 liter cultures were used to inoculate a 500 liter culture. The culture was maintained at 88° C., bubbled with Ar (7.5 liters/min) and stirred at about 50 rpm. After about 20 hours ($A_{600}$~0.5) the cells were harvested with a Sharples continuous flow centrifuge at 100 liters/hour. The cells were frozen in liquid N2 immediately after harvesting. The yield of cells is typically 400–600 g wet weight.

It should be noted that *P. furiosus* has a fermentative type of metabolism and produces organic acids, $CO_2$ and $H_2$ as final products. $H_2$ production inhibits growth, so cultures have to be sparged with Ar (or any inert gas) to remove $H_2$. Alternatively, elemental sulfur may be added. In this case, the reductant that would otherwise be used to generate $H_2$ is used to reduce elemental sulfur to $H_2S$. The addition of elemental sulfur is convenient for small scale cultures in glass vessels, but its reduction cannot be used to remove inhibitory $H_2$ in 500 liter stainless steel fermentors because of the corrosive nature of $H_2S$.

2. Purification of Pf DNA Polymerase I

A. Lysis of Pf Cell Paste

Fifty grams (g) of Pf cell paste prepared in Example 1 were thawed at room temperature. Two hundred milliliters (ml) of lysis buffer consisting of 50 millimolar (mM) Tris-HCl, pH 8.2, 10 mM beta mercaptoethanol, 1 mM EDTA and 200 microgram/ml (µg/ml) of lysozyme were admixed to the thawed cell paste. The admixture was thereafter maintained for 30 minutes at room temperature. The maintained admixture was processed in a French press for two cycles. The cell lysate was sonicated for 10 minutes at room temperature and centrifuged at 16,000 RPM in a SA600 rotor for 60 minutes at room temperature and the supernatant recovered.

B. Column Chromatography of Pf Cell Lysate

The supernatant prepared above was loaded on to a Q-sepharose (2.5×40 centimeter) column at room temperature. The column containing the cell lysate supernatant was then washed with 200 ml of column buffer (50 mM Tris-HCl, pH 8.2, 10 mM beta mercaptoethanol and 1 mM EDTA). The column pass through and the washes were collected, pooled, and then centrifuged at 9000×g in a Sorvall GS3 rotor at room temperature to remove any insoluble material.

The resulting supernatant, containing partially purified Pyro polymerase, was recovered from the pellet and loaded directly onto a phosphocellulose column (2.5×40 cm) at room temperature. The column was washed with column buffer to remove any proteins that did not bind to the column until the optical density measured at an absorbance of 280 nm dropped to baseline. The immobilized Pyro polymerase was thereafter eluted with a one liter linear gradient of NaCl ranging in concentration from 0 M to 0.7 M dissolved in column buffer and 10 ml fractions were collected.

C. Assay for Pfu DNA Polymerase I Activity

The collected fractions were separately assayed for Pyro polymerase activity. The following reagents were admixed to form a reaction cocktail for the measurement of Pyro polymerase activity; final concentrations (fc) of the reagents in the cocktail are in parentheses:

(1) 200 microliters (μl) active calf thymus DNA, 575 μl distilled water, 20 μl 1 M Tris-HCl, pH 7.5 (fc=20 mM); 8 μl 1 M $MgCl_2$ (fc=8 mM);

(2) 10 μl 0.75 M DTT (fc=7.5 mM); 4 μl 15 mg/ml BSA (fc=50 μg/ml);

(3) 30 μl 10 mM each of dATP, dCTP, dGTP dTTP (fc=0.15 mM for each); and (4) 50 μl $^3$H-TTP in ethanol 432A (Amersham Inc., Arlington Heights, Ill.) for a total volume of 1 ml.

To perform the Pyro polymerase (DNA Polymerase I) activity assay, 25 μl of the reaction cocktail formed above was admixed with 1 to 5 ul of each collected fraction. The admixture was maintained for 10 to 60 minutes at 75° C. which was the optimal temperature for enzymatic activity to form a labelled DNA admixture. After the maintenance period, 2 to 5 μl of the labeled DNA admixture was pipetted onto DE81 (Whattman) filter paper. The filter paper containing the labeled DNA admixture was dried on aluminum foil under a heat lamp for 5 minutes. After the drying period, each filter was washed three times for 5 minutes with 50 ml of 2×SSC (0.3 M NaCl, 0.03 M NaCitrate) followed by one quick wash with 100% cold ethanol. The washed filters were immediately placed fresh aluminum foil and placed under a heat lamp for 5 minutes to dry the filters. The dried filters were separately placed in scintillation vials containing 5 ml scintillation fluid.

The $^3$H-DNA immobilized on the filter paper, which reflects Pyro polymerase activity, was measured in a scintillation counter. The results of this assay indicated that the peak fractions from the phosphocellulose column containing the highest concentration of Pyro polymerase were eluted with 200 mM NaCl and that Pyro polymerase constituted about 10% of the total protein present in those fractions.

D. FPLC Purification of Pyro Polymerase

The fractions containing approximately 90% of the total DNA polymerase I activity as measured above were pooled and dialyzed against column buffer overnight at 4° C. to form a NaCl-free Pyro polymerase solution. The dialyzed salt-free Pyro polymerase solution was loaded onto a Mono S HR 5/5 FPLC (fast phase liquid chromatography) column (Pharmacia, Piscataway, N.J.) previously equilibrated with the before-described column buffer. The Mono S column containing the Pyro polymerase was washed with about four column volumes of column buffer prior to elution to remove any proteins that did not bind to the column. The immobilized proteins were eluted with a one liter linear gradient of NaCl ranging in concentration from 0.0 M to 0.7 M dissolved in column buffer.

Fractions were collected and assayed for the presence of FPLC purified Pyro polymerase activity as described, respectively, in B and C above. The results of this assay indicated that the peak fractions from the Mono S column containing the highest concentration of FPLC purified Pyro polymerase were eluted with 120 mM NaCl. The fractions containing 90% of the peak FPLC purified Pyro polymerase activity were pooled and dialyzed against the column buffer additionally containing 10% glycerol overnight at room temperature to form NaCl-free FPLC purified Pyro polymerase.

The resultant purified and dialyzed Pyro polymerase was then subjected to a final purification on a 1.5×20 cm Matrix gel Blue A column (Amicon, Danvers, Mass.). The Matrix gel Blue A column was first equilibrated with the before-described column buffer containing 10% glycerol, 0.1% Tween 20 (polyoxyethylenesorbitan monolaurate) and 0.1% non-idet P40 (octylohenol-ethyl ene oxide condensate containing an average of 9 moles ethylene oxide per mole of phenol). The purified and dialyzed Pyro polymerase was then applied to the column using FPLC pumps. The column containing the Pyro polymerase sample was then washed with two column volumes of the glycerol-containing column buffer to remove any proteins that did not bind to the column. The immobilized Pyro polymerase was eluted from the column with a one liter linear gradient of KCl ranging in concentration from 0.0 M to 0.7 M KCl.

Eluted fractions from the Affi-gel column were collected and assayed for the presence of purified Pyro polymerase activity as described in Examples 2B and C above. The fractions eluted with 200 to 300 mM KCl contained the peak Pyro polymerase activity, with the optimal activity recovered at about 280 mM KCl. The peak fractions were pooled and concentrated through Centricon-30 columns which have a molecular weight cut-off at 30,000 kD (Amicon, Beverly, Mass.) to form a concentrated solution of purified Pyro polymerase. The purified Pyro polymerase was thereafter dialyzed against column buffer containing 50% glycerol to form KCl-free purified Pyro polymerase. The resultant salt-free Pyro polymerase was determined to be about 95% homogeneous.

3. Molecular Weight Determination

The molecular weight of the purified Pyro polymerase prepared in Example 2D was determined by SDS-PAGE under non-denaturing conditions according to the method of Laemmli et al., *J. Mol. Biol.*, (1973) 80:575–599. Samples of Pyro polymerase, Taq polymerase, phosphorylase B, and bovine serum albumin, were applied to a 6–18% gradient, 1 mm thick, SDS-polyacrylamide gel (Novex, Encinitas, Calif.) and electrophoresed in a running buffering containing 1% SDS, 2.4 mM Tris, and 18 mM Glycine. The results of that analysis, shown in FIG. 1, indicate that Pyro polymerase migrates faster than phosphorylase B (Sigma, St. Louis Mo.; molecular weight 97,200 daltons) and Taq polymerase (Perkin-Elmer Cetus, Norwalk, Conn.; 94,000 daltons), but slower than BSA (Sigma, 66,000 daltons). Because of its proximity to Taq, Pyro polymerase was assigned a relative molecular weight of 90,000–93,000 daltons.

4. Fidelity Assays

Various assays were performed to complete the characterization of DNA Polymerase I purified from *P. furiosus*. In the assays described below, the Pyro polymerase was compared to the commercially available and well characterized *Thermus aquaticus* (Taq) DNA polymerase (U.S. Pat. No. 4,889,818).

To determine the error rate of Pyro polymerase, fidelity assays by PCR were performed with the Pyro polymerase in an assay procedure generally described by Kohler et al, *Proc. Natl. Acad. Sci. USA*. 88:7958–7962 (1991), in which in vivo mutagenesis was monitored during PCR amplification of transgenic mouse genomic DNA containing 33 copies per cell of the lacIOZα transgene. The entire lac I gene plus the alpha-complementing fragment of the beta-galactosidase gene was amplified (30 to 40 rounds) by PCR to form amplified DNA. The amplified 1.9 kb DNA was then cloned into the EcoR I site of lambda gt10 and plated on host strain DH5alpha (lacZ▲M15) which contains the alpha fragment of beta-galactosidase.

The complementation of the two proteins resulted in enzymically-active beta-galactosidase, which was detected as blue plaques when X-gal (5-bromo-4-chloro-3-indolyl-beta-D-galactosidase) was present as a substrate. In contrast, a functional non-mutant lac I repressed the expression of beta-galactosidase which resulted in white plaques. The mutation frequency in lac I was defined as the proportion of mutant blue plaques to the total number of plaques scored. The error rate was then calculated by the formula E=2 (mf/d) where mf was the observed mutation frequency in the PCR product (lac I) and d was the number of doublings according to Saiki et al., *Science*, 239:487–491 (1988).

Results from these studies indicate that Pyro polymerase has an error rate (mutations per nucleotide per PCR cycle) as low as $1 \times 10^{-6}$ compared to $1 \times 10^{-5}$ for Taq DNA polymerase as described by Eckert et al., *Nucl. Acids. Res.*, 18:3739–3744 (1990). Thus Pyro polymerase exhibits about a ten-fold greater replication fidelity than Taq DNA polymerase.

5. Exonuclease 3' to 5' Activity Assays

Purified Pyro polymerase, prepared as in Example 2D, was assayed to measure its 3' to 5' exonuclease activity. The exonuclease assay was conducted according to Chase et al, *J. Biol. Chem.*, 249:4545–4552 (1974), except that the reaction was at 72° C. instead of 37° C. and the substrate was Taq I-digested lambda DAN filled in with tritium labelled dCTP and dGTP. Briefly, the following reagents were admixed to form a reaction cocktail for the measurement of 3' to 5' exonuclease activity; final concentrations (fc) of the reagents in the cocktail are in parentheses:

(1) 40 µl 1 M Tris-HCl, pH 7.5 (fc=40 mM);
(2) 10 µl 1 M MgCl$_2$ (fc=10 mM);
(3) 13.3 µl 0.75 M DTT (fc=10 mM);
(4) 100 µl labelled Taq 1 cut lambda DNA filled in with Sequenase™ and labelled with $^3$H dCTP and $^3$HdGTP obtained from Amersham, Arlington Heights, Ill.; and
(5) 636.7 µl distilled water for a total volume of 1 ml.

For the 3' to 5' exonuclease activity assay, 20 to 25 µl of the prepared reaction cocktail was admixed with either Pyro or Taq DNA polymerase. The admixture was maintained for 10 to 60 minutes at 72° C. to form hydrolyzed lambda DNA, specifically $^3$H-5' phosphate mononucleotides. The reaction in each admixture was terminated by admixing 5 µl of 15 mg/ml bovine serum albumin (BSA) and 13 µl of 50% trichloroacetic acid (TCA) and maintaining the admixture on ice for 15 minutes. The terminated reaction admixture was then centrifuged at 12,000×g for 15 minutes to pellet the unhydrolyzed intact lambda DNA.

The resultant supernatant containing the $^3$H-5'exonuclease-derived phosphate mononucleotides was removed from the pellet. Forty µl of each supernatant was admixed with 80 ul distilled water and 1 ml scintillation fluid. The amount of $^3$H radioactivity detected by scintillation counting was a relative measure of the exonuclease activity of the Pyro and Taq DNA polymerase preparations.

The results of this study show that Pyro polymerase exhibits detectable 3' to 5' exonuclease activity, whereas Taq polymerase does not.

To determine the amount of non-specific nuclease activity present in the Pyro polymerase preparation, Pyro polymerase prepared in Example 2D was admixed with 20 to 25 µl of a reaction cocktail. The following reagents were admixed to form the reaction cocktail for the measurement of non-specific nuclease activity; final concentrations (fc) of the reagents in the cocktail are in parentheses:

(1) 40 µl 1 M Tris-Hcl, pH 7.5 (fc=40 mM);
(2) 10 µl 1 M MgCl$_2$ (fc=10 mM);
(3) 13.3 µl 0.75 M DTT (fc=10 mM);
(4) 100 µl $^3$H-labelled *E. coli* chromosomal DNA (sheared ten times through a 21 gauge needle); and
(5) 835.7 µl distilled water for a final volume of 1 ml.

The admixture containing the reaction cocktail and the homogenized gel were maintained for 10 to 60 minutes at 75° C. which was the optimal temperature for the enzyme to form hydrolyzed nucleic acid product. The reaction in the admixture was terminated and supernatant was assayed as described in Example 2C above. The results of this assay show that Pyro polymerase did not exhibit detectable non-specific nuclease activity. The 3' to 5' exonuclease activity by Pyro polymerase is, therefore, specific and not due to non-specific nuclease activity.

Thus, pfu DNA polymerase I is a thermostable DNA polymerase that, unlike Taq DNA polymerase, possesses a 3' to 5' exonucleases activity which enables pfu polymerases to proofread errors, and thereby exhibits a ten-fold greater fidelity during DNA synthesis reactions.

6. PCR with Pyro Polymerase

The specificity of Pyro polymerase was evaluated in PCR amplification of template DNA compared to that achieved with Taq DNA polymerase. To prepare the template DNA for the reactions, genomic DNA was first purified by phenol extraction and alcohol precipitation according to the procedures of Ausubel et al., *Current Protocols in Molecular Biology*, John Wiley and Sons (1987), from blood obtained by tail bleed from a transgenic mouse having about 1 to 2 copies of a lambda transgene vector, which is referred to as lambda transgene mouse genomic DNA.

The lz-lambda polynucleotide primers with the used in the PCR amplifications were prepared by chemical synthesis using a model 381A polynucleotide synthesizer (Applied Biosystems Inc., Foster City, Calif.) according to the manufacturer's instructions.

A hybridization reaction admixture was formed by combining the following reagents in a sterile 0.5 ml microfuge tube:

(1) 80 µl of sterile, autoclaved water;
(2) 10 µl of 10× reaction buffer containing 500 mM KCl, 100 mM Tris-HCl, pH8.3, 15 mM MgCl$_2$, and 0.1% sterile gelatin;
(3) 8 µl of a solution containing 2.5 mM each of the deoxynucleotidetriphosphates (dNTP's) dGTP, dCTP, dTTP, and dATP;
(4) 1 µl of a solution containing 250 ng each of the two polynucleotide primers described above; and
(5) 1 µl of lambda transgene mouse genomic DNA.

The hybridization reaction admixture was heated to 94° C. and maintained at 94° C. for 1 minute to denature the duplex genomic DNA present and form single-stranded templates. The admixture was then cooled to 54° C. and maintained for 2 minutes to allow hybridization to occur and form duplex DNA. The hybridized admixture was thereafter centrifuged in a microfuge at 12,000×g for 10 seconds to collect condensation off the microfuge tube walls. To separate microfuge tubes, 0.5 ul of a solution containing 2.5 units of either Taq DNA polymerase (obtained from Perkin-Elmer Cetus, Norwalk, Conn. or from Stratagene, La Jolla, Calif.) or Pyro polymerase prepared in Example 2D was admixed to form a primer extension reaction admixture. Additional separate primer extension reaction admixtures were made by diluting the amount of Pyro polymerase from 1:1.5, 1:2, 1:2.5, 1:3, 1:4 and 1:5 to determine the optimal concentration of DNA synthesis. (The 1:3 dilution represented about 1.5 unit of Pyro polymerase per microliter.)

Each microfuge tube containing the above-prepared primer extension reaction admixture was overlayed with 50 µl of mineral oil and then place into a DNA Thermal Cycler (Perkin-Elmer Cetus) and subjected to the following temperature and time conditions: 1) 94° C. for 1 minute to denature duplex DNA; 2) cooled to 54° C. for 2 minutes to anneal the primers; and 3) heated to 74° C. for 1.0 minute to activate the polymerase and maintained at 74° C. for 0.5 minutes to extend the annealed primers. The tubes were subjected to 30 cycles of the above sequence according to the manufacturer's instructions. The cycled tubes were then maintained at 72° C. for 10 minutes followed by 4° C. for 12 hours.

The contents of each primer extension reaction admixture were analyzed on a 6% polyacrylamide gel in 1× TBE by loading 35 µl of the admixture sample and 5 µl of 10× sample buffer onto an 8 centimeter gel, electrophoresing the gel at 100V for about one hour followed by staining the electrophoresed gel with ethidium bromide to visualize the electrophoresed nucleic acids.

The results of the electrophoresed PCR amplified lambda transgene mouse genomic DNA using either Pyro or Taq DNA polymerase indicted that the Taq from Cetus and Stratagene gave nearly identical results. The results using the Pyro DNA polymerase to amplify genomic DNA indicate that it produces less background. The 1:2.5 dilution of Pyro polymerase resulted in optimal PCR amplification.

7. Large Scale Preparation of *Pyrococcus furiosus* DNA Polymerase I

The following steps 1–11 are performed at room temperature:

1. Thaw 1500 grams of frozen cell paste at room temperature. Add 4 volumes (6000 mls) of lysis buffer A.

2. Resuspend the cells and incubate at room temperature for 30 minutes. Cycle the cells through a French press two times.

3. Sonicate the product of step 2 for 10 minutes at room temperature. Centrifuge the resulting lysate at 9K RPMs in a GS3 (Sorvall) rotor at room temperature for 60 minutes.

4. Collect the supernatant (Fraction I) and load it directly onto a Q-sepharose (8×30 cm) column. Wash the loaded column with 4 volumes (6 liters) of buffer B.

5. Collect the pass-through and washes. Adjust the collected material to pH 6.0 with HCl, and centrifuge it at 9K in a GS3 rotor at room temperature for 60 minutes to remove the protease-containing precipitate.

6. Collect the supernatant and adjust its pH to 7.8 with NaOH (Fraction II). Load it at 50 ml/minute directly onto a 500 ml radial flow P-11 (phosphocellulose) (Sepragen, San Leandra, Calif.) column equilibrated with buffer B. Wash the column with 1–2 liters of buffer B until the $OD_{280}$ of the wash is back to baseline.

7. Elute DNA polymerase activity with a 0–0.7M NaCl gradient in buffer B (2×2500 ml). The peak of polymerase activity elutes at approximately 0.2–0.4M NaCl.

8. Assay and pool those fractions containing greater than 90% of the total polymerase activity.

All subsequent steps are performed at 4° C.

9. Dialyze the pooled material of step 8 overnight against 200 volumes buffer B at 4° C.

10. Remove the dialyzed Pyro polymerase and clarify it with a 30 minute centrifugation if necessary (Fraction III). Load dialysate onto a heparin-agarose column (5×20 cm) equilibrated with buffer B. Wash with 1 liter buffer B and elute with a 0–0.7M NaCl gradient in buffer B (2×1.5 liters).

11. Assay for polymerase activity, and pool the fractions containing greater than 90% of total activity. Dialyze the recovered material against 200 volumes of buffer C.

12. Remove the Pyro polymerase from dialysis (Fraction IV) and load it onto an Affigel Blue column (2.5×20 cm) equilibrated with buffer C.

13. Wash the Affigel-Blue column with buffer C until the OD 280 approaches baseline and elute the Pyro polymerase with a 0–0.7M KCl gradient in buffer C 2×1000 ml).

14. Assay for polymerase and 3' exonuclease activities. Analyze the active fractions by silver stained SDS-PAGE gels. Pool the pure Pyro polymerase (greater than 90% pure on a w/w basis) fractions based on visual analysis silver stained gel.

15. Dialyze overnight against 200 volumes of buffer D at 4° C. Remove the dialysate (Fraction V) and load it onto an 1.5×30 cm P11 (phosphocellulose) column equilibrated with buffer D. Wash with buffer D until wash OD 280 is baseline. Elute the Pfu DNA PolI with a 2×250 ml linear gradient 0.0–0.7M kCl prepared in buffer D.

16. Assay for polymerase and 3' exonuclease activities. Analyze the active fractions by silver stained SDS-PAGE gels. Pool the pure Pyro polymerase (greater than 95% pure on a w/w basis) fractions based on visual analysis silver stained gel.

17. Pool and dialyze overnight at 4° C. against 20 volumes buffer E. Remove from dialysis (fraction VI) and store at −20° C.

BUFFERS

Buffer A: (6 liters)

| 50 mM | Tris-Cl pH 8.2 |
|---|---|
| 10 mM | beta mercaptoethanol |
| 1 mM | EDTA |
| 200 µg/ml | lysozyme |

Buffer B: (20 liters)

| 50 mM | Tris-Cl pH 8.2 |
|---|---|
| 10 mM | beta mercaptoethanol |
| 1 mM | EDTA |

Buffer C: (6 liters)

| 50 mM | Tris-Cl pH 8.2 |
|---|---|
| 10% | glycerol |
| 1 mM | EDTA |
| 1 mM | DTT |
| 0.1% | tween 20 |
| 0.1% | nonidet P40 |

Buffer D: (2 liters)

| 50 mM | Tris-Cl pH 8.2 |
|---|---|
| 10% | glycerol |
| 1.0 mM | EDTA |
| 10 mM | beta mercaptoethanol |
| 0.1% | tween 20 |
| 0.1% | nonidet P40 |

Buffer E

| 50 | Tris Hcl pH 8.2 |
|---|---|
| 0.1 mM | EDTA |
| 1 mM | DTT |
| 0.1% | Tween 20 |
| 0.1% | NP 40 |
| 50% | glycerol |

RESINS 1.5 LITERS Q-SEPHAROSE (PHARMACIA)
700 MLS P-11 (WHATMANN)
200 MLS HEPARIN-AGAROSE (BIORAD)
200 ML AFFIGEL-BLUE (BIORAD)

8. Production of Pfu I

Cell Growth: *Pyrococcus furiosus* (DSM 3638) was grown at 85–88° C. as closed static cultures in a medium containing maltose (5 g/liter), $NH_4Cl$ (1.25 g/liter) elemental sulfur (S°, 5 g/liter), $Na_2S$ (0.5 g/liter), synthetic sea water (17), a vitamin mixture (18), $FeCl_3$ (25 mM), $NaWO_4$ (10 mM) and yeast extract (1.0 g/liter). Growth was monitored by direct cell count and by the increase in turbidity at 600 nm. For large scale cultures, sulfide was replaced with titanium (III) citrate, and S° was omitted which necessitated sparging with Ar. Two 20 liter cultures served as an innoculum for growth in a 400 liter fermenter where the cultures were maintained at 88° C., bubbled with Ar (7.5 liters/min) and stirred (50 rpm). Cells were harvested after approximately 20 hours ($OD_{600}$-0.5) with a Sharples centrifuge at 100 liters/hour.

NOTE: The following procedures are performed at 25° C., unless otherwise stated.

Cell Lysis: The night before lysis, 500 grams of frozen cell paste is transferred to a 2–8 C refrigerator. The next morning, the cells are transferred to a 4 liter stainless steel beaker. The cells are resuspended using 4 volumes (2000 ml) of lysis Buffer 8A. The cell suspension is then incubated at room temperature for 1.5 hours. The cells are lysed in the French Press using 2 passes at 8K PSI. The lysate is then sonicated at room temperature for 10 minutes.

Following sonication, the lysate is transferred to 400 ml bottles and spun for 60 minutes at 9K rpm at room temperature in the Sorvall RC-2B using a Sorvall GS3 rotor. The supernatant (Fraction I) is collected and the volume measured.

Q-Sepharose Column: Fraction I is loaded directly onto a 8×30 cm radial flow Q-sepharose column (_1500 ml) pre-equilibrated in Buffer 1B at a flow rate of approximately 50 ml/minute. The column is then washed with 4 column volumes (6000 ml) of Buffer 8B.

NOTE: It is important to carefully collect the pass-thru and wash fractions as they contain the Pfu polymerase enzyme The Q-Sepharose pass-thru and column washes are next combined as one pool (Fraction II).

BPA-1000 Precipitation: Bioprocessing aid BPA-1000 (TosoHaas) pilots are conducted on Fraction II to determine the appropriate volume required to precipitate cell debri and nucleic acids but not Pfu polymerase. 1.0 ml aliquots of Fraction II are placed in 8 tubes. The BPA-1000 is mixed thoroughly and 0, 2, 4, 6, 8, 10, 12, 14, 16, 18 and 20 ml of BPA-1000 are added to the tubes respectively, mixed gently, incubated for 5 minutes, and spun in a microfuge for 5 minutes. Carefully decant and save the supernatants. Samples of each tube are then evaluated using the gapped duplex polymerase assay. Evaluate the clarity of each supernatant and the firmness of each pellet. Based on the control tube (without BPA addition), determine which concentration of BPA increases the clarity of the supernatant without sacrificing polymerase yield. The appropriate amount of BPA-1000 is then added to Fraction II and stirred for 30 minutes. The suspension is then transferred to 400 ml centrifuge bottles and spun at 9K rpm at room temperature (25° C.) for 60 minutes in a Sorvall RC-2B using a Sorvall GS3 rotor. The supernatant (Fraction III) is collected and the volume measured.

Fraction III is then adjusted to pH 7.5 with 1 N HCl if necessary.

P-11 Cellulose Column: Fraction III is loaded directly onto a 10×14 cm P-11 column (˜1000 ml) pre-equilibrated in Buffer 8C at a flow rate of approximately 5 ml/minute. The column is washed with Buffer 8C until the $OD_{280}$ approaches baseline (4 column volumes). The column is next eluted with a 2×4000 ml gradient (0 to 700 mM KCl) prepared in Buffer 8C. 25 ml fractions are collected, every fifth tube, put-on and pass-thru are assayed for polymerase activity. The fractions containing the peak of Pfu Pol I activity are pooled and concentrated to approximately 200 ml using an Amicon model $CH_2$ concentrator with a SIY30 membrane cartridge. Any remaining Pfu Pol I is washed from the concentrator by flushing the lines with an additional 300 ml Buffer 8C. The concentrate and wash are combined (Fraction IV).

NOTE: The following procedures are performed at 4° C.

Fraction IV is next dialyzed overnight against 18 liters of Buffer D.

Hi-Load S Column: The following morning the dialysate is transferred to 400 ml centrifuge bottles and spun 9K rpm at 4° C. for 60 minutes in a Sorvall RC-2B using the GS3 rotor. The supernatant (Fraction V) is recovered and the volume recorded. Fraction V is divided into two equal portions. The first portion is loaded directly onto a FPLC Hi-Load S column (˜58 ml) pre-equilibrated in Buffer D at a flow rate of 5.0 ml/minute. The column is washed with Buffer 8D until the $OD_{280}$ approaches baseline. The column is next eluted with a 2×250 ml gradient (0 to 250 mM KCl) prepared in Buffer D. 5.0 ml fractions are collected, every third tube, put-on and pass-thru are assayed for polymerase activity. The above procedure is repeated for the second portion of Fraction V. The fractions containing the peak Pfu Pol I activity are pooled and dialyzed overnight against 2×4 liters of Buffer 8E at 4 C. The following morning, the dialysate is removed from dialysis and the volume recorded (Fraction VI).

Heparin Sepharose CL-6B Column: Fraction VI is loaded onto a 1.5×90 cm heparin sepharose CL-6B column (˜159 ml) pre-equilibrated in Buffer 8E at a flow rate of 0.5 ml/minute. The column is washed with 1000 ml Buffer 8E. The column is next eluted with a 2×750 ml gradient (0 to 300 mM KCl) prepared in Buffer 8E. 10 ml fractions are collected, every third tube, put-on and pass-thru are assayed for polymerase activity. A protein gel is also recommended for peak evaluation. The fractions containing the peak Pfu DNA polymerase activity are pooled and dialyzed overnight against 2×4 liters of Buffer 8E. The following morning, the dialysate is removed from dialysis and the volume recorded (Fraction VII).

Affi-Gel Blue Column: Fraction VII is loaded onto a 2.5×4.0 cm affi-gel blue column (˜20 ml) pre-equilibrated in Buffer 8E at a flow rate of 0.5 ml/minute. The column is washed with Buffer 8E until the $OD_{280}$ approaches baseline. The column is next eluted with a 2×500 ml linear gradient (0 to 250 mM KCl) prepared in Buffer 8E. 10 ml fractions are collected, every third tube, put-on and pass-thru are assayed for polymerase activity. A SDS-PAGE gel is also recommended for careful peak evaulation. The fractions containing the peak Pfu Pol I activity are pooled and dialyzed overnight against 1 liter final dialysis Buffer SF. The following morning, the purified enzyme is removed from dialysis and transferred to −20° C. storage and represents a purified pfu polymerase I enzyme of this invention.

| Buffer 8A: Lysis Buffer | |
|---|---|
| 50 mM | Tris-Cl, pH 8.2 |
| 1 mM | EDTA |
| 10 mM | b-mercaptoethanol |
| 200 mg/ml | lysozyme |

-continued

Buffer 8B: Q-Sepharose Buffer

| 50 mM | Tris-Cl, pH 8.2 |
|---|---|
| 1 mM | EDTA |
| 10 mM | b-mercaptoethanol |

Buffer 8C: Phosphocellulose Buffer

| 50 mM | Tris-Cl, pH 7.5 |
|---|---|
| 1 mM | EDTA |
| 10 mM | b-mercaptoethanol |

Buffer 8D: High Load S Buffer

| 50 mM | Tris-Cl, pH 7.5 |
|---|---|
| 1 mM | EDTA |
| 1 mM | DTT |
| 10% (v/v) | glycerol |
| 0.1% (v/v) | NP-40 |
| 0.1% (v/v) | Tween 20 |

Buffer 8E: Affigel Blue & Heparin Buffer

| 50 mM | Tris-Cl, pH 8.2 |
|---|---|
| 1 mM | EDTA |
| 1 mM | DTT |
| 10% (v/v) | glycerol |
| 0.1% (v/v) | NP-40 |
| 0.1% (v/v) | Tween 20 |

Buffer 8F: Final Dialysis Buffer

| 50 mM | Tris-Cl, pH 8.2 |
|---|---|
| 0.1 mM | EDTA |
| 1 mM | DTT |
| 0.1% (v/v) | NP-40 |
| 0.1% (v/v) | Tween 20 |
| 50% (v/v) | glycerol |

9. Cloning the Gene that Encodes *Pyrococcus furiosus* (Pfu) DNA Polymerase I

*Pyrococcus furiosus* (DSM 3638) was grown as described by Bryant et al, *J. Biol. Chem.*, 264:5070–5079 (1989), with an additional supplement of 10 mM Na$_2$WO$_4$ as described in the Examples. Following harvesting by centrifugation, genomic DNA was isolated from the biomass using Stratagene's genomic DNA isolation kit according to manufacturer' instructions. The DNA was then randomly sheared by several passages through an eighteen gauge needle and the fragments were separated by sucrose gradient centrifugation. The size of the fragments present within the fractions of the sucrose gradient were next estimated by agarose gel electrophoresis. The fractions containing four to nine kilobase fragments were combined and ligated to EcoR1 linkers and the resulting inserts were ligated into EcoR1 cut Lambda Zap II vector (Stratagene, La Jolla, Calif.) to create a genomic *Pyrococcus furiosus* library. This library was plated with XL1-Blue *E. coli* (Stratagene) on LB plates. Plaque lifts were performed on Duralose nylon filters (Stratagene) to isolate individual bacteriophage colonies containing a cloned insert.

N-terminal amino acid sequence determination of pfu I purified as described in Example 2 was performed by the Wistar Institute. Briefly, partially purified protein was subjected to SDS-PAGE followed by electrotransfer to a nylon membrane. The band corresponding to Pfu polymerase was isolated and subjected to protein microsequencing. From this microsequencing analysis, the unambiguous sequence of the forty-eight N-terminal amino acids of the pfu polymerase I protein was determined. The 48 residues corresponds to residues 1 to 48 of SEQ ID NO 1. Internal amino acid sequence analysis was also performed by the Wistar Institute on tryptic digested fragment of the Pfu polymerase protein.

Based on the N-terminal 48 amino acid residue sequence information, a series of degenerate PCR oligonucleotide primers were designed in pairs which would produce a 94 basepair (bp) PCR product. The 94 bp product corresponds to amino acid residues within the 48 residues. These oligonucleotides (23 and 18 bases corresponding to the two ends of the 94-mer) were designed such that the 3' terminal 8 nucleotides of every sequence possible based on the known amino acid residue sequence within the 48 residues was present as a separate oligonucleotide. The 23-mer corresponds to possible nucleotides at positions 224 to 246, and the 18-mer corresponds to possible nucleotides at positions 300 to 317. Whenever there was a wobble position in the rest of the oligonucleotide primer, a T was used. The rationale for these substitutions was based on the fact that the GC content of pfu is considerably low and that T mismatches are most tolerated by Taq polymerase. In this way, four oligos were needed for each of the two primer positions. Each of these oligos contained some mismatched bases but no degenerate positions.

The PCR was performed on pfu genomic DNA with all 16 possible primer pairs. Following agarose gel electrophoresis, it was determined that 12 of the 16 amplification reactions produced the expected 94 bp PCR product. One of the reactions containing the 94 bp product was subjected to direct cycle sequencing (Stratagene) using both PCR primers used in the amplification reaction as sequencing primers. A 53 base sequence deduced from the DNA sequencing gel was found to corresponded 100% to the known N-terminal amino acid sequence between a pair of primers, thus confirming that the sequence was from the gene encoding Pfu DNA polymerase. A 53 base oligonucleotide probe containing this sequence was next synthesized, and having the nucleotide sequence shown in SEQ ID NO 2 from nucleotides 247 to 299. This oligonucleotide was then end labelled with $^{32}$P and used to screen the Pfu genomic library. Approximately four *Pyrococcus* genomes were represented in the screened library. The probe was hybridized to plaque lifts at 42° C. for two hours in QuikHyb (Stratagene) and washed twice at room temperature for 15 minutes each in 2×SSC 0.1% SDS. Thirteen putative clones were identified and the plaques cored and resuspended in 300 ml SM. Ten ml of each lysate was transferred into 1× Taq reaction buffer, heated to 100° C. for ten minutes, and 30 cycles of PCR was performed using the PCR primer pair which originally produced the expected 94 bp fragment (PCR was performed according to the procedure described in the GeneAmp kit [Cetus Perkin-Elmer]). Following electrophoretic analysis of the PCR products, three clones produced the expected 94 bp PCR product. These three lambda clones were excised into to a pBluescript plasmid (Stratagene) according to the manufacturer's protocol. The resulting transformants were then screened by PCR. PCR was performed on single colony transformants (100° C. in 1× Taq reaction buffer for 10 minutes, then centrifuged briefly followed by 30 cycles of PCR using the original primer pair and the procedure described in the GeneAmp kit. Three positive plasmid clones were identified from each excision and large scale plasmid preparations were performed on one colony from each clone.

The three bonafide polymerase clones were next mapped. One had a relatively small 1500 bp insert. The other two clone inserts were about 4500 basepairs; one containing about 1000 bp of the Pfu polymerase sequence while the other clone contained the entire polymerase gene. The clone having the entire pfu polymerase I gene was named pF72.

The insert of clone pF72 was sequenced on both strands using Sequenase™ (USB) and custom oligonucleotide primers using a primer walking strategy. The sequence of the polymerase gene is shown in SEQ ID NO 2 from nucleotide bases 224 to 2548, and consists of a 2265 bp DNA seqment encoding 775 amino acids corresponding to a 90,113 Dalton protein.

The Pfu gene can be cloned into an expression system for production of the recombinant protein. The complete coding region of the pfu polymerase I gene is PCR-amplified using Pfu polymerase to limit mutations and the PCR product product is ligated in reading frame into the vector pRSET (Invitrogen). The ligated vector is transformed into an F' containing E. coli host strain and protein production is induced with a recombinant M13 phage expressing cloned T7 RNA polymerase under control of the lacUV5 promoter. The expression vector is designed to introduce an affinity tail which can be used to facilitate purification of the recombinant protein. Following cell lysis and clarification of the crude supernatant, the recombinant Pfu polymerase protein is isolated in a single step by metal affinity chromatography.

In another strategy, the coding region of the Pfu DNA polymerase gene is amplified with Pfu polymerase using primers which introduce a unique restriction site at the ends of the PCR product to facilitate cloning into a pBluescript vector. When cloned into the T3 orientation, the protein is expressed under control of the lacZ promoter. Following expression, recombinant Pfu polymerase is purified with a modification of the procedure used to purify the native enzyme. Briefly, a heat precipitation step is employed following cell lysis and clarification. The heat precipitation step denatures and precipitates the majority of *E. coli* host proteins but not the thermostable Pfu polymerase and the remaining soluble fraction is recovered and used as described before as a source for purification of the pfu polymerase I protein.

The foregoing is intended as illustrative of the present invention but not limiting. Numerous variations and modifications can be effected without departing from the true spirit and scope of the invention.

What is claimed is:

1. An isolated polynucleotide encoding a thermostable DNA polymerase, wherein the isolated polynucleotide is capable of hybridizing to a polynucleotide complementary to a polynucleotide that encodes amino acids 1 to 775 of SEQ ID NO: 1 under hybridization conditions comprising incubating at 42° C. in a hybridization buffer comprising 0.9 M NaCl and 50% formamide, and under wash conditions comprising incubating at 68° C. in a wash buffer comprising 0.015 M NaCl and 0.5% sodium dodecyl sulfate.

2. The isolated polynucleotide of claim 1, wherein the thermostable DNA polymerase is a fusion protein.

3. A vector comprising the isolated polynucleotide of claim 1.

4. A host cell comprising the isolated polynucleotide of claim 1.

5. A method of preparing a recombinant thermostable DNA polymerase, comprising culturing the host cell of claim 4 under conditions suitable for the expression of the thermostable DNA polymerase.

* * * * *